(12) United States Patent
Kronberg

(10) Patent No.: US 10,086,198 B1
(45) Date of Patent: Oct. 2, 2018

(54) ELECTROSTIMULATION PRINCIPLE, METHOD AND DEVICE FOR IMPEDANCE CHANGE THEORETICALLY ENHANCING CALCIUM-CALMODULIN BINDING

(71) Applicant: APOGEE MEDICAL, LLC, Dunwoody, GA (US)

(72) Inventor: James W Kronberg, Dunwoody, GA (US)

(73) Assignee: APOGEE MEDICAL, LLC, Dunwoody, GA (US)

( * ) Notice: Subject to any disclaimer, the term of this patent is extended or adjusted under 35 U.S.C. 154(b) by 230 days.

(21) Appl. No.: 14/881,036

(22) Filed: Oct. 12, 2015

Related U.S. Application Data

(60) Provisional application No. 62/062,505, filed on Oct. 10, 2014.

(51) Int. Cl.
*A61N 1/36* (2006.01)
*A61N 1/04* (2006.01)
*A61N 1/32* (2006.01)

(52) U.S. Cl.
CPC ....... *A61N 1/36014* (2013.01); *A61N 1/0464* (2013.01); *A61N 1/0468* (2013.01); *A61N 1/326* (2013.01)

(58) Field of Classification Search
CPC .............. A61N 1/36014; A61N 1/0464; A61N 1/0468; A61N 1/326
See application file for complete search history.

(56) References Cited

U.S. PATENT DOCUMENTS

| | | |
|---|---|---|
| 5,217,009 A | 6/1993 | Kronberg |
| 5,413,596 A | 5/1995 | Kronberg |
| 6,011,994 A | 1/2000 | Kronberg |
| 6,321,119 B1 | 11/2001 | Kronberg |
| 6,535,767 B1 | 3/2003 | Kronberg |
| 7,117,034 B2 | 10/2006 | Kronberg |
| 7,840,272 B2 | 11/2010 | Kronberg et al. |
| 8,159,312 B2 | 4/2012 | Kronberg |
| 8,785,196 B2 | 7/2014 | Kronberg et al. |
| 2011/0160811 A1* | 6/2011 | Walker ................ A61H 39/002 607/72 |

* cited by examiner

*Primary Examiner* — Lindsey G Wehrheim
(74) *Attorney, Agent, or Firm* — Smith Tempel; Steven P. Wigmore

(57) ABSTRACT

A bioelectric signal generation and application method generates a signal that comprises a succession of pulses arranged either in continuous trains or in separated bursts; in which each pulse within a train or burst comprises at least three distinct intervals of time; in which the first said interval of time has one definite polarity and sufficient current density and duration to cause motion of calcium ions ($Ca^{++}$) in relation to less strongly charged components of a body, cell or tissue, such as proteins and especially the protein calmodulin (CaM); in which the second said interval of time has substantially zero current density and is of sufficient duration to allow any proteins or other molecules which became distorted by electric fields present during said first interval, and especially CaM, to relax back into their normal, undistorted shapes, said first and second intervals of time thus comprising a "two-step electric process."

26 Claims, 10 Drawing Sheets

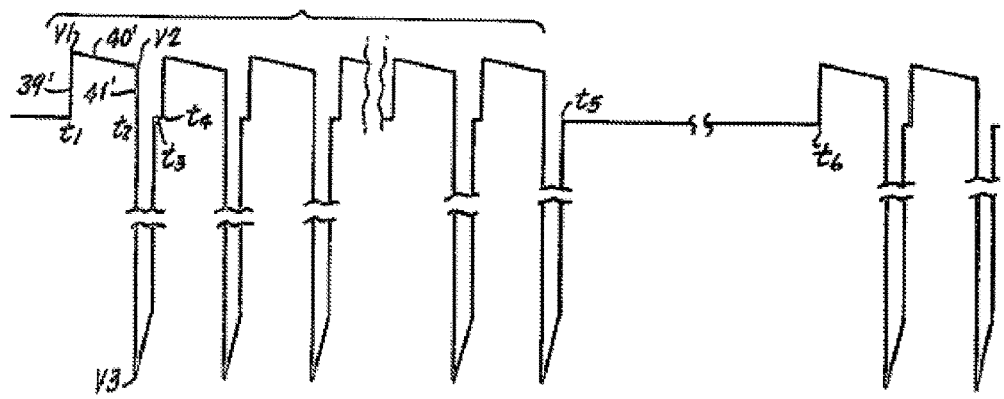
Figure 1a - CONVENTIONAL ART
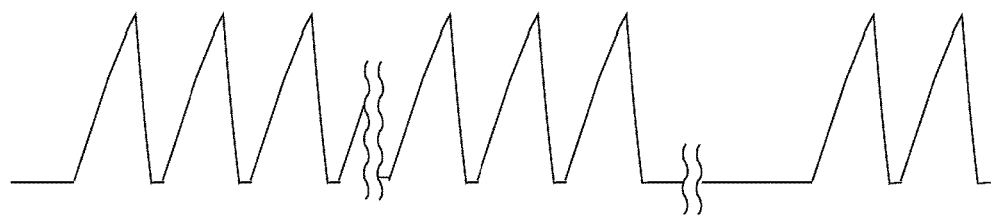
Figure 1b - CONVENTIONAL ART

ELECTROSTIMULATION PRINCIPLE, METHOD AND DEVICE FOR IMPEDANCE CHANGE THEORETICALLY ENHANCING CALCIUM-CALMODULIN BINDING

FIELD OF THE INVENTION

This disclosure relates to the electrical treatment of biological tissue. In particular, what is disclosed is a device that produces discrete electrical pulse trains for treating osteoporosis and accelerating bone growth, for reducing pain and swelling, and for slowing or reversing degenerative changes in cells and tissues, through a specific "two-step electric process" comprising (1) first applying a voltage gradient through a biological material sufficient to cause ion movement, followed immediately by (2) reducing the gradient to near zero for a sufficient period to permit ion-binding sites, and especially the calcium-binding sites of calmodulin, to recover from any field-induced distortion and resume their optimal conformations for such binding.

BACKGROUND

Human bone, cartilage and other tissues contain components such as hydroxyapatite, a complex calcium phosphate ($Ca_5(PO_4)_3OH$) in crystalline form, and the protein collagen, which are piezoelectric; that is, which generate electric fields when mechanically stressed. In addition, the flow of fluids through vessels or intercellular spaces within tissues can also generate electric fields, so-called "streaming potentials." In living tissue, these fields drive electric currents through the intercellular fluid creating electric potentials across the cell membranes, which may either activate receptors there directly, cause motion of ions increasing their probability of bonding to receptor sites, and/or open voltage-gated ion channels permitting motion of ions such as calcium into the intracellular medium to bond with receptors there.

Based upon research conducted in the 1960's and '70's, it appears that these electric fields are important, if not essential, to the maintenance of tissue integrity and good health, and to the repair of damage and degenerative changes which may result in whole or in part from their absence. A striking example is disuse osteoporosis, which results from limb immobilization for example while in traction or in a cast. In the absence of electric fields caused by normal use, the bone loses calcium and becomes brittle. The application of an electric field with an appropriate waveform, timing and strength from outside the body can easily prevent or reverse this form of degeneration.

Studies conducted by C. A. L. Basset, John Ryaby, Arthur Pilla and others during the 1960's and '70's identified a range of waveforms, strengths and timings with the potential to reverse osteoporosis, to accelerate the healing of broken bone, and to restart and complete the healing of nonunion fractures: those which have failed to complete healing on their own. It is believed that on the cellular level, and especially at the very small scale of processes occurring at cell membranes, these artificial signals replicate at least some of the properties of the body's own, naturally generated signals.

FIG. 1a shows the waveform induced in tissue by a pulsed electromagnetic field (PEMF) as used in early bone healing stimulators based on the work of Bassett, Pilla and others. This figure exactly reproduces FIG. 5b in U.S. Pat. No. 4,105,017, "Modification of the Growth, Repair and Maintenance Behavior of Living Tissue and Cells by a Specific and Selective Change in Electrical Environment, by John P. Ryaby and Arthur A. Pilla, issued Aug. 8, 1978. This is the waveform called "Mode 2" in that patent.

It may be noted that since this waveform represents a differential voltage, the choice of polarity shown is arbitrary and the waveform could equally well be represented by the same graph flipped top to bottom. In addition, since in PEMF the induced waveform in tissue is actually the first derivative of that in the coils, the original waveform applied to the coil is a triangle wave as shown in FIG. 1b. Since without an iron core induction at the frequencies used is quite inefficient, this triangle waveform must be applied to the coils at a power level which is orders of magnitude higher than that desired in the tissues.

The waveform comprises a sequence of pulse bursts, each nominally five milliseconds long, repeated preferably between 5 to 15 bursts per second, and separated by interburst periods of substantially no signal. Adopting the same identifying characters used in U.S. Pat. No. 4,105,017, one such burst extends from time t1 to time t5, as indicated by the brackets at the top of the figure, while the following interburst period extends from t5 to t6. A small portion of another such interburst period is shown prior to t1, while following t6, a small portion of another such burst is shown.

Within each burst of the Ryaby-Pilla "Mode 2" waveform, each individual pulse comprises three distinct phases.

A relatively long pulse, shown as positive in FIG. 1, extends from t1 to t2 with a nominal duration of about 200 microseconds. The voltage intensity within this pulse is relatively constant, with a preferred value between 1 and 3 millivolts per centimeter in the treated tissue.

This is followed by a shorter phase with the opposite polarity, shown as negative in FIG. 1, extending from t2 to t3. This phase is nominally 30 microseconds long, and may have a relatively constant intensity or one changing more or less rapidly over time, so long as the maximum intensity does not exceed about 50 millivolts per centimeter in the treated tissue.

Yet a third pulse component, containing substantially zero current, extends from t3 to t4 with a nominal duration of 10 microseconds, and represents a short "break" or "rest" at the end of each pulse before the next arrives. No mention of this third component appears in the patent claims, and Arthur Pilla has stated that it was not expected to play a role in the stimulation process. In any waveform generator driving an inductive load, as in the Ryaby-Pilla design, such a "break" may be added as a safety margin to ensure that the current from one pulse has dropped to zero before the next pulse is triggered, so successive pulses do not overlap and partly cancel each other.

Calcium-modulated protein, usually abbreviated "calmodulin" or simply "CaM," is a small protein comprised of 148 amino acids, typically found either bound to cell membranes or free-floating in the cytoplasm near them. Its usual role is to respond to changes in the concentration of intracellular calcium ion ($Ca^{++}$), which is a biochemical second messenger with many roles in the body. About twenty varieties of CaM are known, having the same overall structure but differing slightly in the details of their amino-acid sequences.

As shown schematically in FIG. 2, in the absence of $Ca^{++}$, CaM normally takes a "dumbbell-shaped" conformation 100 comprising seven helical regions 102a through 102g, of which region 102d is by far the longest and forms the shaft of the dumbbell. Helical regions 102a through 102g are joined end-to-end by short flexible intermediate chains 104a through 104f.

Of these short chains, four of them 104a, 104c, 104d and 104f (together with the ends of the helices adjoining each of them) comprise two close-set pairs of "EF-hand" regions. An EF-hand comprises about ten amino acids at the end of a first helix; a short flexible chain of twelve amino acids at least six of which have negatively-charged side chains, such as glutamate and aspartate; and about ten amino acids at the start of a second helix. When the protein molecule is undistorted, for example by external electric fields, the helices at each end of an EF-hand are approximately perpendicular to each other while the negative side chains geometrically surround a vacant center just the right size to accept and tightly bind a $Ca^{++}$ ion while rejecting other small positive ions with a high degree of specificity. (Celio, Pauls and Schwaller, Guidebook to the Calcium-Binding Proteins, © 1996, Oxford University Press.) These binding sites are indicated in FIG. 2 by dashed circles 106a through 106d.

Slight differences between their amino-acid sequences cause the $Ca^{++}$ affinities and binding time constants of the four EF-hand sites to differ, so the four ions are bound sequentially and with increasing $Ca^{++}$ concentration the majority of CaM may either be free or have one, two, three or all four sites filled. With each ion bound, CaM's conformation changes until when all four sites are filled by $Ca^{++}$ ions 108a through 108d respectively, CaM takes instead a "horseshoe" conformation 110 with long helix 102d now separated into two portions 112a and 112b and folded like a hinge. Thus folded, the CaM molecule can wrap around and bind to a target domain 114 of any one of a large number of enzymes, thereby activating (or in some cases, deactivating) the enzyme. $Ca^{++}$-CaM binding therefore lies at the start of a host of biochemical pathways within the body.

Arthur Pilla and others have proposed $Ca^{++}$-CaM binding as the primary means by which electric signals within the body, when not strong enough to stimulate nerves, can still be transduced into biochemical signals. Because cytoplasm and extracellular fluids are electrically conductive while cell membranes are substantially insulating, electric fields in tissue are concentrated at and near such membranes, often exceeding the average fields in tissue by several orders of magnitude. CaM is typically located near or physically bound to such membranes.

Since CaM on the whole is approximately neutral electrically, while $Ca^{++}$ is strongly charged, an electric field will cause $Ca^{++}$ to move while CaM, especially if membrane-bound, remains nearly stationary. This will cause some of the $Ca^{++}$ to collide with, and bind to, CaM. The PEMF waveform described in U.S. Pat. No. 4,105,017 was designed, based upon knowledge of $Ca^{++}$-CaM binding kinetics, to optimize this effect causing increased binding and enzyme activation.

Since the EF-hand regions of CaM are more negatively charged than other parts of the molecule, in an electric field these regions are drawn more strongly in the direction of positive charge with resulting distortion of the molecule, as shown (again schematically) by structure 120 in FIG. 3 where all EF-hand regions 106a through 106d have been displaced in the same direction (shown in the Figure as upward) with respect to the rest of the molecule. Since helices in a protein molecule, here 102a through 102g, are relatively rigid, flexing occurs primarily in the short joining chains, with accompanying distortion of the EF-hand binding sites 106a through 106d likely impacting their ability to bind $Ca^{++}$ or the kinetics or specificity of such binding. To indicate this loss or impairment of function, in FIG. 3 each binding site is indicated by a broken dashed circle rather than by a complete one as in FIG. 2.

Since CaM's primary role is to respond to changes in $Ca^{++}$ concentration in the absence of electric fields, evolution appears to have favored structural variants in which optimal binding and maximum specificity for $Ca^{++}$ takes place when the molecule is undistorted, while increasingly strong external fields and the resulting distortion cause increasingly less effective binding and lower specificity. The fact that the amino-acid sequence of calmodulin is strongly conserved across widely-separated species, particularly in the EF-hand regions (see for example Yang, Prokaryotic calmodulins, J. Mol. Microbiol. Biotechnol. 3(3): 457-459 (2001)), together with the geometric requirement that the helices flanking an EF-hand region be approximately perpendicular and the fact that electrical distortion of the molecule will change this angle, suggest that the molecule's sensitivity to such distortion could be quite high, with a negative impact on its functionality.

As a result, an electric field could be expected to act in either of two, mutually opposing ways: either enhancing $Ca^{++}$ binding through ion motion, or discouraging it by distorting CaM binding sites making ion capture more difficult or selection less specific to $Ca^{++}$. At low field intensities, with CaM still relatively undistorted, a roughly linear increase in $Ca^{++}$ binding would be expected with increasing field strength. At some point, however, molecular distortion would begin to outweigh the effects of ion motion. $Ca^{++}$ binding would peak, then drop off with further increases in signal strength, and ultimately fall below the level occurring with no field present.

This, in fact, is the case.

FIG. 4 illustrates typical dose-response curves for cell or tissue electrostimulation taken from two classic journal articles. (It may be noted that neither of these used a Pilla-type PEMF.) Since the amplitudes of the applied signals cover four orders of magnitude plus zero, a power-law scale was used on the horizontal axis. The vertical axis, representing the response level, is linear with the 100% level representing response of the control which had no signal applied.

Curve 150 shows ATP (adenosine triphosphate) production in response to a DC signal (Cheng et al., The effects of electric currents on ATP generation, protein synthesis and membrane transport in rat skin. Clin. Orthop. 171, 264-272 (1983)). Curve 152 shows glycine uptake in response to the same field. Both have the same form with an initial increase, passage through a maximum, then a steady decrease crossing the control level as the field strength increases, with the highest-field effects opposite to those seen at low fields. This is much the same pattern seen with most vitamins, minerals and prescribed drugs, in which small amounts are necessary for health but larger amounts can be toxic or otherwise damaging.

Curves 154 and 156 show cell response with a pulsed AC signal applied (Korenstein et al., Capacitively pulsed electric stimulation of bone cells: Induction of cAMP changes and DNA synthesis. Biochim. Biophys. Acta 803, 302-307 (1984)). For easy comparison, the signal levels of all curves have been converted to common units. Data for the AC signal were reported only for controls and at three relatively high signal levels. The dashed, low-signal portions of these curves were inferred from the slopes of lines connecting the published data points and from the fact that both responses were defined as 100% at zero signal.

Curve 154 shows cyclic adenosine monophosphate (cAMP) synthesis in response to the AC signal. cAMP synthesis is initially inhibited by stimulation, reaches a minimum, then increases until it crosses the control level and thereafter is increased. This is simply the same pattern seen in curves 150 and 152, but inverted.

Curve 156 shows DNA synthesis in response to the same AC signal. At low signal intensities it follows the same pattern as curves 150 and 152, first rising to a maximum and then declining. Upon reaching the control level, however, the curve rebounds and rises again. This suggests that there may be two different and opposing mechanisms or biochemical cascades involved, one showing stimulation and the other inhibition by the applied signal, with curve 156 representing the sum of the two. The low-signal mechanism for DNA synthesis likely involves CaM, while the high-signal mechanism may not.

Surprisingly, when all results are converted to common units of signal intensity, all of the initial deviations reach their peak values (maxima for curves 150, 152 and 156; a minimum for curve 154) at approximately the same signal level, between 10 and 100 microamperes per square centimeter. Moreover, all curves either cross or, in the case of curve 156, rebound from, the control level again at approximately the same signal level, between about 200 and about 500 microamperes per square centimeter, as indicated by dashed oval 158. This argues for a common mechanism underlying all four responses shown.

For comparison, the commonly accepted "strength-duration" or "S-D" curves as used in the present practice of electrotherapy are shown in FIG. 4b. These show the thresholds of response of various nerve types in a typical user when stimulated by isolated electric pulses of varying lengths ("durations") and intensities ("strengths"). The curves were redrawn from Nelson, Hayes and Currier, Clinical Electrotherapy, Third Edition (Appleton & Lange, 1999) but for easy comparison with FIG. 4, the X and Y axes were reversed and the total applied current was converted to current density (the same as in FIG. 4) by assuming the stimulating signal was applied over a skin area of 100 square centimeters.

For pulses longer than about 1000 microseconds (one millisecond) the nerve response depends only on the pulse strength, while as pulses grow increasingly shorter below this limit they require correspondingly higher intensities to achieve like effects. At a signal strength below curve 160, usually nothing is felt. Such a signal is termed "subthreshold." Above curve 160 there will normally be some sensation. Muscle stimulation begins at curve 162. At curve 164 most users begin to perceive the signal as painful, while at curve 166 most find the pain intolerable.

It is notable that the peak effects from a cell-stimulating signal fall below the sensory threshold indicated by curve 160, and thus in the subthreshold region, while the vast majority of prior art electrostimulators are intended to stimulate nerves of one type or another and thus by definition use signals whose strengths lie well above at least one of the thresholds shown. As was indicated in FIG. 4a, such strong signals are far from optimal for cell or tissue stimulation and, if used in hope of such a result, may in fact have effects opposite from those desired.

Combining Arthur Pilla's suggestion that it is electric-field-caused motion of $Ca^{++}$ striking CaM which leads to increased binding and is the primary means by which relatively weak electric signals within the body are transduced into biochemical signals, with the hypothesis that CaM inherently binds $Ca^{++}$ most readily and selectively when no such field is present, suggests that maximum binding will take place in response to a two-step electric process: first the application of a relatively strong field to bring $Ca^{++}$ and CaM into close proximity at or near a cell membrane, then brief removal of the field so CaM can relax into its undistorted conformation for optimal $Ca^{++}$ binding before the ions disperse or an oppositely-directed pulse phase draws them away again.

Depending upon its strength, the molecular environment and the $Ca^{++}$ concentration, the optimal length for application of the relatively strong field may range from several tenths of a microsecond upward to several tens, hundreds or even thousands of microseconds, with an optimal value probably in the vicinity of thirty microseconds for practical field strengths in most tissues. CaM relaxation and $Ca^{++}$ binding are then expected to take a further interval, again ranging from several tenths of a microsecond upward depending upon the molecular environment of the CaM and the available $Ca^{++}$ concentration, with an optimal value probably in the vicinity of ten microseconds in most tissues. Only when this process is substantially complete should an electric field, directed either in the preceding direction or, usually more practically, in the opposite direction so as to create a zero-net-charge (ZNC) signal, be re-introduced.

PEMF, as stated above, stands for "pulsed electromagnetic fields" and was the original approach taken to apply weak pulsed electric fields to cells and tissues to stimulate healing, relying on electromagnetic induction to create the fields through the mechanism of eddy currents. This approach, although found safe and effective in close to a million treatment cases to date, remains grossly inefficient in terms of power since relatively large currents must flow through a coil to induce the much smaller signals actually performing the stimulation. This makes even the newest generations of PEMF devices undesirably heavy, bulky and costly.

A more direct and often preferable manner of signal delivery, using PEF or "pulsed electric fields," was described by Kronberg in U.S. Pat. No. 5,217,009 (1993), U.S. Pat. No. 5,413,596 (1995), U.S. Pat. No. 6,011,994 (2000), U.S. Pat. No. 6,321,119 (2001), U.S. Pat. No. 6,535,767 (2003), U.S. Pat. No. 7,117,034 (2006), and published applications #2006/0293724 (2006) and #2008/0039901 (2008), all of which are hereby incorporated by reference.

With PEF, the signal in treated tissue is generated not by electromagnetic induction, but instead by applying a pulsed controlled voltage or current having substantially the same waveform as that desired in the tissues. It is applied to the target tissues through electrodes, preferably noninvasively through the skin. If signals are applied so as to set up the correct current densities in the treated tissues, taking into account their resistivities and geometry, this approach can induce the same waveforms at the cell and tissue level as in PEMF but with much greater power efficiency, at lower device cost, and often with improved user convenience.

All of the cited Kronberg patents and published applications disclose signals of the same general form, in which a continuous pulse train or a succession of pulse bursts comprises individual pulses each having just two phases, differing in length and having opposite polarities. These signals are meant to be applied to the intact human body, human tissue in vitro, an animal body or animal tissue in vitro, cultured tissue, cultured cells or other biological material, for the purpose of stimulating healing, cell or tissue repair or regeneration, cell proliferation, cell differentiation, enhanced synthesis of desired substances such as proteins, ATP, growth factors, nitric oxide or other biochemical messenger substances, or other applications as will be found by reading the cited patents.

FIG. 5, which reproduces a part of FIG. 4 in U.S. Pat. No. 5,217,009, shows a typical Kronberg waveform in a format easily compared with that of FIG. 1 in this present application. Here interval T1 corresponds exactly to Pilla's interval t1-t2, interval T2 to Pilla's interval t2-t3, interval T3 to Pilla's interval t1-t5 comprising the entire pulse burst, and interval T7 to Pilla's interval t5-t6 comprising substantially no signal. Intervals T5 and T6 at the start and end of each burst, much like Pilla's interval t3-t4, result from circuit characteristics but are not expected to have any physiological significance. Interval T4 is a charge-equalizing pulse following the burst to achieve zero net charge. Within each individual pulse there are only two intervals or phases, one positive corresponding to interval T1 and Pilla's interval t1-t2 and the other negative corresponding to interval T2 and Pilla's interval t2-t3, without any "break" or "rest" corresponding to Pilla's interval t3-t4.

Pulses comprising intervals T1 and T2 may optionally be applied instead as continuous trains not including intervals T3 through T7.

All of the cited Kronberg patents were based on the assumption that one or more conventional CMOS (complementary metal-oxide-semiconductor) logic gates or similar switching devices, in which the output must represent either a logic "1" (high) or a logic ("0" (low) voltage, would be used to form the device output. Such a device, regardless of the type of electronic switching elements actually used, appears as a switch with only two possible positions: one connected to a relatively more positive voltage level representing logic "1" or "high," the other to a relatively more negative voltage level representing logic "0" or "low."

For example, in a CMOS inverter, the simplest possible logic gate as shown by 170 in FIG. 6, two complementary enhancement-mode MOSFET's (metal-oxide-semiconductor field-effect transistors), a p-channel MOSFET 172 and an n-channel MOSFET 174, have the gates of both connected as an input 176 and the drain terminals of both connected as an output 178, while the source terminals of the p-channel and n-channel devices are tied to the positive supply rail 180 and the negative supply rail 182 respectively.

Applying a logic "1" or "high" to input 176 turns on the n-channel MOSFET while turning off the p-channel one, thus connecting output 178 to negative rail 182 and outputting a logic "0" or "low." Conversely, applying a logic "0" or "LOW" to input 176 turns on the p-channel MOSFET while turning off the n-channel one, thus connecting output 178 to positive rail 180 and outputting a logic "1" or "high." Applying an intermediate input level will turn on both the n-channel and p-channel MOSFET's weakly, thus both generating an indeterminate output (not guaranteed by the manufacturer) and wastefully allowing current to pass directly from the positive to the negative rail, so such intermediate-level input signals are normally avoided. This behavior is shown on graph 190 in FIG. 6b, in which the horizontal axis 192 indicates input voltage, curve 194 indicates the resulting output voltage, and curve 196 indicates the current.

Such a device may be conceived as a simple two-position mechanical switch 184, as shown in FIG. 7a. For clarity, the identifying characters in the following description are identical with those of corresponding parts of the MOSFET circuit which was drawn out in FIG. 6a. A movable contact 178 now forms the output, and can connect either with a positive rail 180 or a negative rail 182. Which position it takes is controlled by the voltage applied at input 176.

If two such switches 184a and 184b are connected to opposite ends of a load 186, such as a human or animal body, tissue or other biological material, as shown in FIG. 7b, the load sees a "differential" output representing the difference between discrete outputs 178a and 178b. This differential output may lie in any of three different regimes of applied voltage and resulting current.

With switch 184a "high" and switch 184b "low," the left side of load 186 will be more positive than the right side and conventional (positive) current will flow from left to right. With switch 184a "low" and switch 184b "high," the opposite will be true. With both switches "low," or with both "high," no voltage will appear across the load and no current will flow.

This third regime, with both switches alike either "high" or "low," might initially appear to offer a simple way of implementing the "two-step electric process" described above for optimum $Ca^{++}$ binding to CaM: first the application of a relatively strong field to bring $Ca^{++}$ and CaM into close proximity, then brief removal of the field so CaM can return to its optimal $Ca^{++}$-binding conformation before the ions disperse or an oppositely-directed pulse phase draws them away again. These two steps would be simply the application of a first- or second-regime signal—that is, either with output 178a high and output 178b low, or vice-versa—followed by a third-regime signal either with both output high or with both of them low.

On human or animal skin, however, the continued application of direct current, or of a signal containing net charge—that is, in which the integral of current over a sufficiently long time does not converge to zero—causes irritation and in time can lead to chemical burns through electrolytic changes in the skin covered by the electrodes. Analogous effects take place in the vicinity of electrodes placed in cell or tissue cultures. For this reason, zero net charge (ZNC) signals are strongly preferred in any PEF-type application.

The Kronberg patents cited above use two different but complementary approaches to achieve zero net charge. First, at the end of each pulse burst a charge-equalizing pulse, which was shown as T4 in FIG. 5, is added with timing chosen to carry substantially the same amount of charge which remains unbalanced at the end of the burst. Second, physical protection is added in the form of DC-blocking, back-to-back electrolytic capacitors. (Multiple capacitors are needed both to provide electrically symmetrical operation and, in a medical product, to assure safety in case of the failure of any single component.) The result is a modified output circuit as shown in FIG. 7c, the same as before except for the addition of capacitors 188a and 188b.

While essential to avoid possible user injury in case of electronic failure, the DC-blocking capacitors have an undesired side effect in normal operation, in that during each pulse burst they store energy in the form of an unbalanced charge. Most of this charge is removed by the equalizing pulse following the burst, leaving a small and usually negligible amount to drain away through load 196 during the following interval of "substantially no signal" indicated by T7 in FIG. 5.

During the burst, however, a significant amount of charge builds up and this means that, if both output switches are connected to the same output rail (whether positive or negative) and thus to each other, the current in load 186 will not be zero, but instead will be determined, and powered, by the stored charge on the output capacitors as indicated by looped arrow 190. This capacitor-driven loop current will appear in the load even when third-regime (both-high or both-low) switch settings are used as portions of nominally charge-balanced signals such as those shown in U.S. Pat. No. 7,117,034, for example in its FIGS. 6 and 7, since during any third-regime interval the loop current 190 decays asymptotically toward, but never actually reaches, zero.

As a result, no signal or waveform disclosed in any of the cited Kronberg prior-art patents or other known prior art successfully implements the "two-step electric process" described above for optimum $Ca^{++}$ binding to CaM. For this process to be effective, immediately following the application of current to bring $Ca^{++}$ and CaM into close proximity, the current must be reduced substantially to zero, eliminating any capacitor-driven loop current, sufficiently long for CaM to return to its undistorted "natural" configuration best suited for binding the $Ca^{++}$.

As a sign of the importance of this failure to implement the described "two-step electric process" in prior Kronberg patents—since at the time they were written, its importance had not yet been recognized—the long history of success of PEMF bone-healing devices using the Pilla waveform in FIG. 1, which serendipitously includes an approximation to the described "two-step electrical process," may be contrasted with the sometimes impressive but highly inconsistent results from experimental devices based on the Kronberg patents. For example, the MedRelief SE-60, a device closely based on that described in U.S. Pat. No. 6,535,767, was tried in 2006 and 2007 by MedRelief, Inc. in an 84-subject, randomized controlled study on osteoporosis, measuring bone mineral density and biochemical markers for bone formation over eight months of PEF treatment of the spine. The PEF waveform induced in tissue by the SE-60 differs from the Pilla waveform shown in FIG. 1*a* chiefly through lacking Pilla's third pulse interval of substantially zero current, shown as interval t3-t4. While some patients in the study showed impressive recovery of spine mineral density, others did not, and the study as a whole failed to reach statistical significance on any of the outcome variables.

The inability to implement the described "two-step electrical process," now thought necessary for optimal $Ca^{++}$ binding to CaM initiating biochemical cascades leading to pain relief and healing, is common to the devices described in all of the cited Kronberg patents to date, due to the requirement for switching devices in which the outputs must represent a combination of logic "1" (high) and logic ("0" (low) states.

The present invention is meant to remedy this deficiency, now that it has been recognized: providing a simple yet robust and widely applicable means of implementing the "two-step electronic process" described above in any application of pulsed electric field (PEF) treatment of humans, animals, tissues, cells or other biological material.

SUMMARY OF THE DISCLOSURE

The invention comprises a bioelectric signal generation and application method in which the signal comprises a succession of pulses arranged either in continuous trains or in separated bursts; in which at least one pulse within a train or burst comprises at least three distinct intervals of time; in which the first said interval of time has one definite polarity and sufficient current density and duration to cause motion of calcium ions ($Ca^{++}$) in relation to less strongly charged components of a body, cell or tissue, such as proteins and especially the protein calmodulin (CaM); in which the second said interval of time has substantially zero current density and is of sufficient duration to allow any proteins or other molecules which became distorted by electric fields present during said first interval, and especially CaM, to relax back into their normal, undistorted shapes, said first and second intervals of time thus comprising the "two-step electric process" described above; in which the third said interval of time has one definite polarity opposite that of the first said interval of time and contains approximately equal charge, having either a like duration and the same (although oppositely directed) intensity, or otherwise; and in which the fourth said interval of time, if present, again has substantially zero current density and is of sufficient duration to allow any proteins or other molecules which became distorted by electric fields present during said third interval of time, again to relax back into their normal, undistorted shapes, said third and fourth intervals of time thus comprising again the "two-step electric process" described above; in which said signal is intended for application to biological material comprising but not limited to the human or animal body, tissue or tissues, or cells; in which said application is through electrodes, such as skin-contact electrodes, or by other conductive means with no reliance on electromagnetic induction; and in which the purpose of said application is one or more of stimulating healing, cell or tissue repair or regeneration, cell proliferation, cell differentiation, enhanced synthesis of desired substances such as proteins, DNA, RNA, ATP, cell or tissue growth factors, bone morphogenetic proteins, nitric oxide, cAMP or other biochemical messenger substances, or applications as will be found by reading the cited previous Kronberg patents; together with newly-described preferred embodiments in the form of electronic circuitry for carrying out said signal generation and application.

The principle of the "two-step electric process" as previously described in this document, in which an electric field is first applied to a body, cell, tissue or other biological material for a first interval of time, in order to move $Ca^{++}$ in relation to less strongly charged components of the material, especially CaM, and then substantially removed for a second interval of time so that proteins or other molecules distorted by the field can relax back into their normal, undistorted shapes, with CaM especially resuming its undistorted shape for optimal $Ca^{++}$ binding, is an important and unique feature of the invention. The optimal length of each interval in the "two-step electric process" is determined in any given case by the field strength, $Ca^{++}$ concentration, molecular environment of CaM, and other factors. Typical lengths for practical signals lie in the range from 0.1 microsecond to 10,000 microseconds, with the most preferable values likely lying between 5 and 100 microseconds.

The inclusion within at least one pulse of a train or burst of at least one iteration of the described "two-step electric process" is yet, one important feature of the invention.

Impedance is defined as the change in voltage across an electric or electronic device, or combination of such devices, needed to cause the current through the device or combination to increase by a defined amount. In a resistor, this is a constant equal to the resistance—the number of volts needed to produce a current change of one ampere—throughout the range of positive and negative voltages over which the resistor is designed to operate. For an open switch (one placed in its "off" position), and disregarding leakage currents, the impedance is effectively infinite. For a closed switch (one placed in its "on" position), the impedance is very low and can often be assumed to be zero. For some other device types, the impedance may change with the voltage applied or may be changed by some external control signal.

The implementation of the described "two-step electric process" by switching the signal generator output impedance between a relatively low and a relatively high state—that is, by applying, during the first interval of time as described above, an approximately constant, non-zero voltage through a relatively low-impedance connection between the signal generator and the biological material to which the signal is to be applied, thus creating the desired electric field in the biological material, and then, during the second interval of time as described above, changing the connection to an "off" or high-impedance state, thus substantially blocking any current flow between the signal generator and the biological material and removing the electric field—is another important feature of the invention.

In order to eliminate capacitor-driven loop current during said second and, if present, said fourth interval, the output loop, as was shown in FIG. 7c, must be broken. This means that at some point in the loop, either in switch 184a or switch 184b or elsewhere, either the connection must be broken physically, or some one or more components must be capable of switching into a sufficiently high-impedance state to prohibit the capable passage of the loop current 190, thus breaking the connection electronically, as will be explained in the material which follows. In order to break and re-form the connection at the speed required for the invention, electronic switching is required. This switching may be either active, through the use of one or more components placed in the signal path and switched between high-impedance and low-impedance states by an external control signal, or passive, in which one or more components placed in the signal path perform such switching inherently, entering a high-impedance state as the voltage sweeps through a defined, narrow voltage range close to zero while having low impedance to signals with voltages outside this range.

The provision of one or more such electronic components within the loop, capable of passively changing or being actively changed between low-impedance and high-impedance states, and electrically placed in the signal path, is another important feature of the invention.

FIG. 7d shows the previously described circuit but modified to add an active impedance-changing capability. Each of switching devices 184a and 184b, again for consistency and simplicity conceived as simple mechanical switches although now understood actually to be electronic, is now modified to have not two but three possible positions: the original pair of "high" and "low," plus a third position 192a or 192b in which it makes contact with neither "high" nor "low" and thus is "off," producing high impedance.

For control of the signal intensity, a resistive element or combination of such elements, here represented by a single resistor 194, is desirably placed in series with load 186. This, together with the voltage applied between supply rails 180 and 182, determines the current passing through load 186 and thus the voltage gradient established within it during each low-impedance phase of the applied pulse burst or pulse train. Both this voltage, and the resistance of element or elements 194, are preferably made high enough to "swamp out" any expected differences in the combined resistive-capacitive impedance of load 186, so that regardless of such differences a substantially known and constant current is applied during each such phase. One or more of elements 194 may be made adjustable, or switching means may be provided to select from among a plurality of such elements, in order to select one of a plurality of such possible current values or one from a continuous range of such values.

FIG. 7d further indicates the ability to perform the described "two-step electric process" with an applied field, during the first step, of either positive or negative polarity. For simplicity, only a circuit implementing this capability with active impedance switching is shown, although in principle it could equally well be done with passive impedance switching.

While the choice of which polarity is positive in FIG. 7d is arbitrary, it will be assumed for the purpose of this discussion to be that in which the left connection to load 186 is more positive than the right connection, and conventional (positive) current thus flows from left to right. This will occur when electronic switch 184a makes connection with the positive supply rail 180, while electronic switch 184b makes connection with the negative supply rail 182. Conversely, when electronic switch 184a makes connection with the negative supply rail 182 and electronic switch 184b makes connection with the positive supply rail 180, the left connection to load 186 will be more negative than the right connection and the polarity of the signal will thus be assumed to be negative. When either of electronic switches 184a and 184b is instead in an "off" state making connection with neither rail, substantially no current flows in load 186.

The optional inclusion within each pulse of two iterations of the described "two-step electric process," said two iterations differing in that their applied electric fields have opposite polarities, is also another important feature of the invention.

FIG. 7e again shows the circuit of FIG. 7c, but this time modified instead to add a passive impedance-switching capability. For this to provide usefully long intervals of high impedance, the rise and fall time between positive and negative phases in a pulse may need be slowed to produce a ramp-like, exponentially decaying or other transition in which the voltage changes relatively slowly as it passes through the region near zero.

For example, and as shown in FIG. 7e, a passive R-C delay may be added by placing another capacitive element or combination of such elements, here represented by capacitor 188c, as a shunt around load 186 and a resistive element or combination of such elements, here represented by a single resistor 194, in series with both capacitive element 188c and load 186. Resistor 194, or some one or more resistive elements in a combination of such elements, may also help to provide current control to load 186 as described above. This results in an exponentially decaying voltage transition across load 186, as shown by trace 200a in FIG. 7f.

Other means for slowing the transitions, for example replacing switches 184a and 184b with linear devices such as operational amplifiers configured so as to produce waveforms with ramp-like transitions, may of course also be used. For example, a comparable waveform produced by operational-amplifiers configured as integrators is shown by trace 202a in FIG. 7f. Note that it is a simple matter, if desired, to give the ascending and descending ramps different slopes as shown through proper choice of the external, passive integrator components, as is well-known in the art of analog circuit design.

Once the passage of the signal voltage through the near-zero region has been made sufficiently slow, the impedance may be rendered high during such passage by placing a nonlinear switching element or combination of such elements, here represented by Zener diode symbol 196 in FIG. 7e, in series with load 186. Such an element has a relationship of current to voltage such that for voltages below some value there is little to no current and thus the impedance is high, while above this value the current increases rapidly resulting in low impedance. This value is often called the cut-in voltage. The response is often asymmetrical, with a low cut-in voltage in one direction (commonly called "forward") and another, which may be unusably high, in the other direction (commonly called "reverse"). In such a case, two separate devices may need to be placed in parallel, head to tail, so the combination has usably low cut-in voltages in both directions.

For example, the voltage-to-current relationship of a generic diode is shown by trace 204a in FIG. 7f, where the horizontal axis indicates voltage and the vertical one indicates current. At forward cut-in voltage 206a the slope of the trace changes from almost flat on the side toward zero voltage, to relatively steep on the opposite side. The same happens at the reverse cut-in voltage 206b. In region 208 between the two cut-in voltages, the nearly flat slope indicates little or no current change with voltage, and thus high impedance. Outside this region, the steeper slopes show large current changes with voltage and thus, low impedances.

Trace 204b, shown as a dashed line where it differs from trace 204a, shows the response of two diodes placed in parallel, head to tail, so the forward cut-in voltage 206c of the second diode replaces the reverse one of the original, single diode.

For a signal with sufficiently slow transitions through the near-zero region, if such a nonlinear device is placed in the signal path there will be a definite time interval during which the signal voltage passes through near-zero region 208 and thus experiences high impedance, while otherwise a low impedance appears and the signal passes unchanged apart from some loss of voltage equal to the cut-in voltage of the conducting device. For simplicity, in traces 200a and 200b the two cut-in voltages are indicated simply by dashed horizontal lines, and zero voltage by a solid line. During signal passage through nonlinear device 196, that part of the waveform with voltages lying between the cut-in voltages is removed and the remaining parts of the waveform "collapse" into the region it occupied, meeting at the zero line, as shown by traces 200b and 202b respectively.

Nonlinear electronic devices potentially usable for this purpose include, but are not necessarily limited to, the following:

| Device type | Typical cut-in voltage | |
| --- | --- | --- |
| | Forward | Reverse |
| Germanium diode | 0.3 volt | 50 volts |
| Silicon Schottky diode | 0.4 volt | 100 volts |
| Silicon junction diode | 0.7 volt | 500 volts |
| Gallium arsenide diode or LED | 1.2 volts | 25 volts |
| Gallium phosphide diode or LED | 1.9 volts | 25 volts |
| Gallium nitride diode or LED | 2.8 volts | 25 volts |
| "Mixed III-V" diode or LED | 1-4 volts | 25 volts |
| Silicon Zener diode | 0.7 volts | 1.8 to 5 volts |
| Silicon avalanche diode | 0.7 volts | 5 volts and up |
| Diac (bidirectional thyristor) | 30 volts and up* | 30 volts and up* |
| MOV (metal-oxide varistor) | 18 volts and up* | 18 volts and up* | in which "mixed III-V" indicates any compound containing three or more of the elements from Group IIIa (boron, aluminum, gallium, indium and thallium) and Group Va (nitrogen, phosphorus, arsenic, antimony and bismuth) in the Periodic Table, including at least one element from each group. For example, most visible-light-emitting diodes are made from mixed III-V materials, such as gallium aluminum arsenide phosphide (GaAlAsP).

Device types indicated by asterisks ("*") in the table above are those which in presently marketed forms have both forward and reverse cut-in voltages too high for use in the present invention, but in theory could be made with lower ones and if so, would be potentially usable in the present invention. Such devices find their most common present use as surge protectors.

In theory, any device which can be fabricated in silicon, such as a Schottky or Zener diode, can also at least in theory be fabricated in any of the other materials listed, as well as in emerging, special-purpose or laboratory semiconducting materials such as diamond, graphene, carbon nanotubes, compounds or alloys of elements from Group IVa (carbon, silicon, germanium, tin and lead), compounds of elements from Group VIa (oxygen, sulfur, selenium and tellurium) with other elements such as transition metals, and nano-structures containing any of the above materials. The scope of the invention includes these possible alternatives as well as those shown in the table.

Any series combination of any of these device types is also potentially useful if the sum of their cut-in voltages has a desirable value. For example, two silicon diodes could be connected in series, both facing in the same direction, so their combined cut-in voltage would be 0.7+0.7=1.4 volts.

The electronic capability to switch the signal generator's output, within the timing structure of a single output pulse, between a low-impedance state, having a definite desired polarity and the ability to source or sink sufficient current to induce the electric field in the first step of the described "two-step electric process," and a high-impedance state as just described, either actively or passively, resulting in substantially zero output current and zero voltage gradient in tissue thus implementing the second step in the described "two-step electric process," is also another important feature of the invention.

FIG. 8 illustrates examples of pulse trains in which the described "two-step electric process" appears, respectively, once in each pulse of the train in FIG. 8a, as indicated by 210 in one such pulse, followed by a charge-balancing phase 212 of longer duration but lower intensity; and twice, with opposite polarities at substantially equal durations and intensities as indicated by 210a and 210b, in each pulse of the train in FIG. 8b. In each case solid lines indicate voltages established across the load at low impedance, while dashed lines indicate the zero level established with high impedance and thus substantially no current delivered to the load, together with the transitions into and out of this state. For simplicity all pulses are shown with abrupt transitions, although it is to be understood that the waveform effects described will also appear with ramped, exponentially decaying or other slowed transitions as well.

FIG. 8c shows the same pulse train as FIG. 8b, but with a time-varying, low-frequency component added as shown by the overall rise and fall of the pulse envelope. It should be noted that the zero-current level established in the load at high output impedance, as indicated in one place by 214, coincides with the true zero level indicated by line 216 and is substantially unaffected by the amplitudes of the preceding and following pulse phases including any such low-frequency component.

For comparison, FIG. 8d shows an analogous waveform created according to Kronberg U.S. Pat. No. 7,117,034, in which a putative "zero" level is established by setting both driver outputs to nominally equal voltages while still at low impedance. Since capacitor-driven loop currents may still be present, however, this nominally "zero" level 218, here represented by a solid line since like the nominally positive and negative phases it is also at low impedance, may actually change both in magnitude and in polarity compared with true zero line 216 since it has a fixed relationship with the other low-impedance voltage levels.

The ability to manipulate the relative, nonzero output voltage or current levels during the first and third intervals of time within a pulse comprising either three of four intervals of time as previously described, while during the second and (if present) the fourth said interval the impedance is made high allowing substantially no output current or voltage, and/or to manipulate the relative lengths of said first and third intervals, so as to achieve substantially equal but opposite transfers of charge within said first and third intervals thereby creating a signal which overall has substantially zero net charge should it be desired, is yet another important feature of the invention.

The ability to manipulate the quantities just described, but in a different fashion so that the transfers of charge are deliberately made not equal and opposite and some charge imbalance remains, producing an overall nonzero net charge should it be desired, is also another important feature of the invention.

The ability to manipulate the quantities just described so as to establish any desired lengths, and ratios of lengths, among the positive, negative, and high-impedance portions of any pulse within a pulse burst or pulse train, and of the lengths and repetition rates of such pulse bursts, by suitable choice of timing intervals sent to the electronic switching devices represented by 184a and 184b in FIG. 7, is an important feature of the invention.

In order to establish the desired current density (as shown by peak effectiveness in the curves in FIG. 5a) in any one of a variety of body locations and resulting tissue cross-sections through which the signal must pass, it is desirable to regulate or stabilize the current intensity as measured in microamperes, and to adjust this level depending upon the body location of treatment. This may be done by changing either the voltages supplied to the switching devices, the resistance placed in the signal path in series with the load, or both.

For the average patient, lacking medical or engineering training, it may be desirable to start the signal at a relatively high level so as to lie above the sensory threshold as shown by curve 160 in FIG. 4b, producing a noticeable sensation; to have this level adjustable by the patient, compensating for individual differences in sensitivity, so as to achieve a noticeable signal intensity without exceeding the pain threshold as shown by curve 164 in FIG. 4b; and then, after a short time, to have the device automatically drop the signal back to a lower, subthreshold level chosen for peak effectiveness as indicated by the curves on FIG. 4a. The higher signal level may optionally then be returned intermittently for brief periods during treatment as a signal to the user that the device is still working. Again, these changes may be accomplished by changing either the voltages supplied to the switching devices, the resistance placed in the signal path in series with the load, or both.

The ability to manipulate the intensity of the signal applied to the load, through proper selection, adjustment, or a combination of selection and adjustment of the voltages supplied to the switching devices and the resistance placed in series with the load, is another important feature of the invention.

The inclusion of DC-blocking capacitors in the signal path, in order to correct any charge imbalance remaining after the described alternation in polarities and manipulation of current, voltage and interval duration for substantially zero net charge, should it be desired, along with components capable of being switched to high impedance to prevent any charge on these capacitors from driving undesired currents through the biological material to be treated, is also another important feature of the invention.

It will be obvious to a person skilled in the art of signal design that the foregoing description of the pulses comprising either three or four consecutive intervals of time, and alternating between high- and low-impedance states so as to include at least one iteration of the described "two-step electric process," can readily be extended to larger numbers of intervals within a single pulse or within successive pulses or successive bursts of pulses. All such extensions to numbers of intervals greater than four, so long as at least one high-impedance and at least one low-impedance interval are included and alternate within some repeating cycle of the signal thereby constituting at least one but potentially any desired number of iterations of the "two-step electric process," regardless of the length of this cycle, are included within the invention. Further, it may be found preferable to have such intervals of time have different durations, applied currents or voltage when simultaneously treating different tissues or acting upon different components within a single tissue, and thus to alternate intervals within a pulse, in successive pulses or successive bursts as described. The ability to construct composite signals of this type, and the flexibility in implementation and use which this ability provides, especially when implemented under microprocessor or microcontroller control, are important features of the invention.

Signals including the described "two-step electric process" may be applied to a human or animal body through readily-available skin-contact electrodes, such as those intended for use with prior art muscle stimulators or transcutaneous electronic nerve stimulators (TENS). Such electrodes are preferably placed at skin locations typically having lower-than average electrical resistance, such as trigger points or acupuncture points (see for example Reichmanis et al., Laplace plane analysis of impedance between acupuncture points H-3 and H-4, Comp. Med. East and West V, 3-4, 289-295 (1977)). Alternatively, said signals may be applied through electrodes penetrating the skin or implanted beneath the skin surface, or through a combination of surface and implanted electrodes. The ability to apply said signals through either of these electrode types, singly or in combination, is another important feature of the invention.

When signals including the described "two-step electric process" are applied to a human or animal body through electrodes, the volume of tissue receiving the majority of the signal energy takes roughly the form of a football with its ends at the electrode locations. Properly choosing electrode locations, for example using charts of trigger points or acupuncture points, to lie at the ends of such a football-like shape allows substantially any volume of tissue in the body to be selected for treatment. The ability to select the tissue volume to be treated, through proper choice of electrode locations, is yet another important feature of the invention.

The ability to generate signals including the described "two-step electric process" from a relatively low-voltage, compact and lightweight source of direct current, such as a battery, is an important feature of the invention. Of course other sources of power, such as AC-to-DC power converters including "wall wart" type modular power supplies, photovoltaic cells, fuel cells, or resonant wireless power transfer could also be used.

Other features and advantages of the present invention will be apparent to those skilled in the art from a careful reading of the Detailed Description of a Preferred Embodiment presented below and accompanied by the drawings.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

In the Figures, like reference numerals refer to like parts throughout the various views unless otherwise indicated. For reference numerals with letter character designations such as "102A" or "102B", the letter character designations may differentiate two like parts or elements present in the same Figure. Letter character designations for reference numerals may be omitted when it is intended that a reference numeral to encompass all parts having the same reference numeral in all Figures.

FIGS. 1a-1b show a conventional art PEMF waveform used for the stimulation of bone tissue.

DETAILED DESCRIPTION

The word "exemplary" is used herein to mean "serving as an example, instance, or illustration." Any aspect described herein as "exemplary" is not necessarily to be construed as preferred or advantageous over other aspects.

Figure 2:
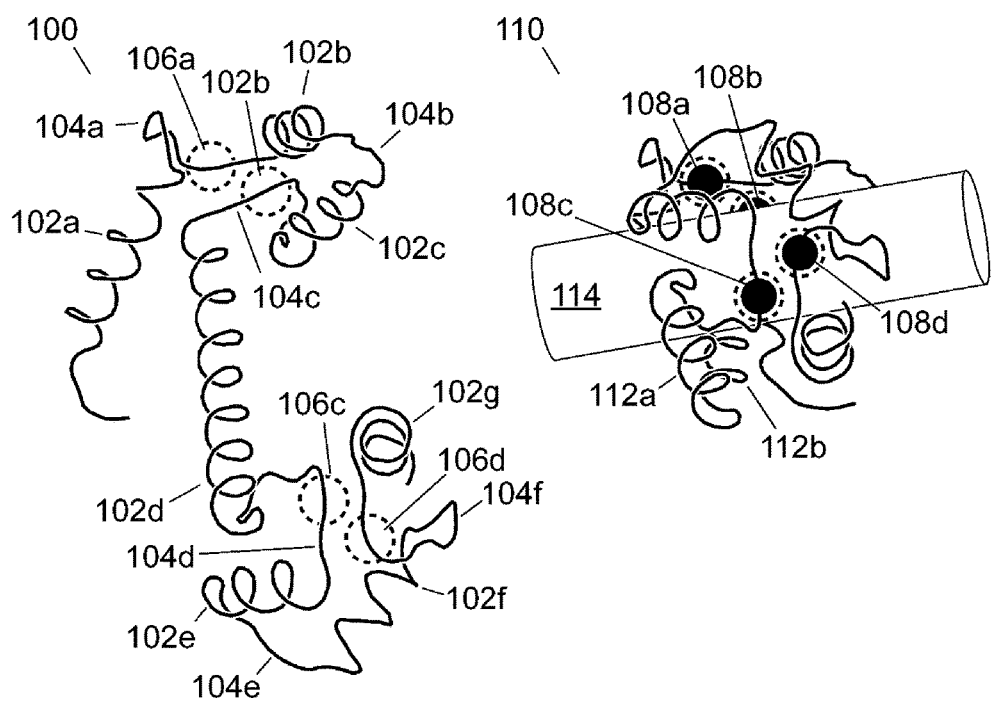
FIG. 2 shows two possible conformations of the protein calmodulin (CaM).
Figure 3:
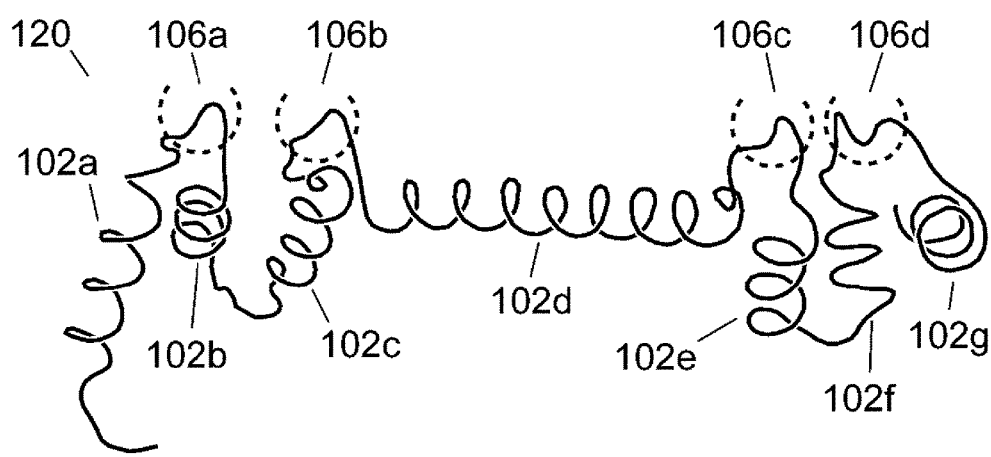
FIG. 3 shows a third possible conformation of the protein calmodulin when exposed to an electric field.
Figure 4A:
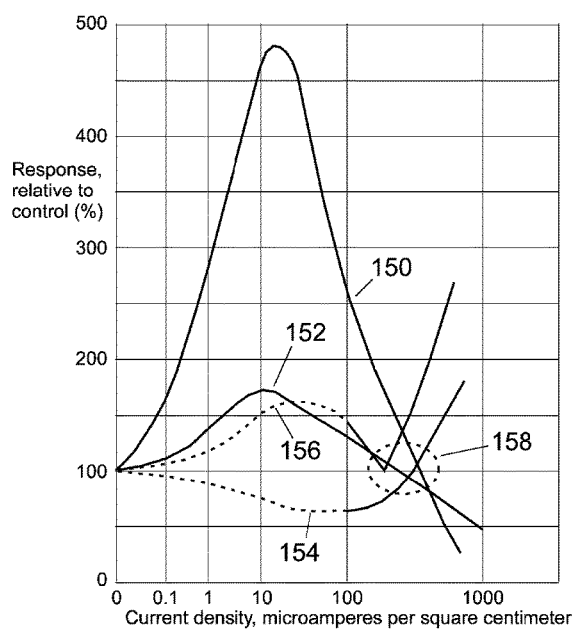
FIGS. 4A-4B show dose-response curves of cells in vitro and nerve thresholds in vivo for electrostimulation.
Figure 4B:
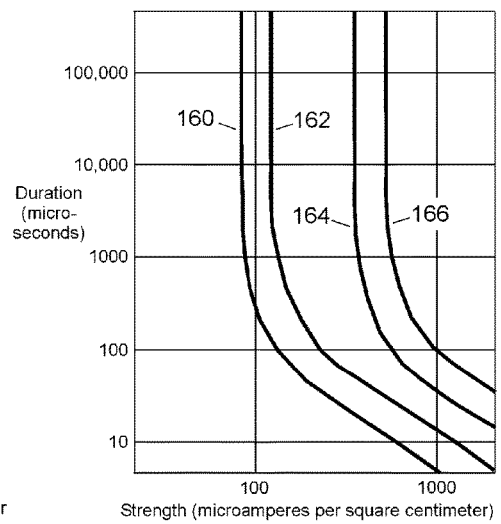
Figure 5:
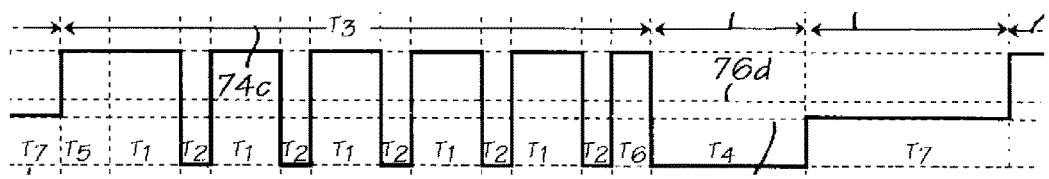
FIG. 5 shows a prior art PEF waveform used for electrostimulation.
Figure 6:
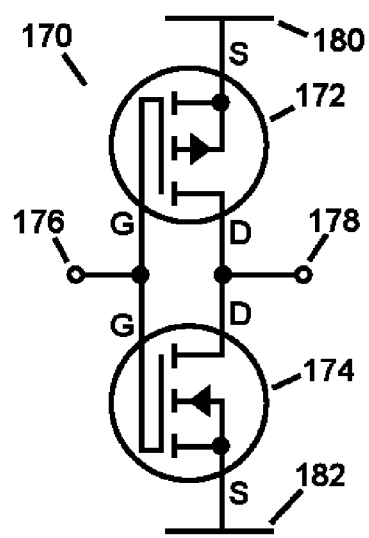
FIG. 6 shows a simple CMOS inverter circuit as used in prior art electro stimulators.
Figure 7A:
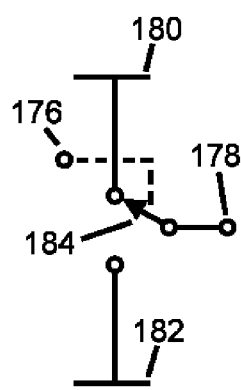
FIGS. 7a-7f show exemplary conceptual designs for output switching circuits and resulting waveform traces.
Figure 7B:
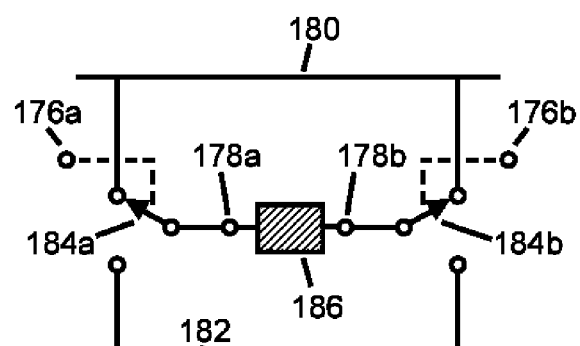
Figure 7C:
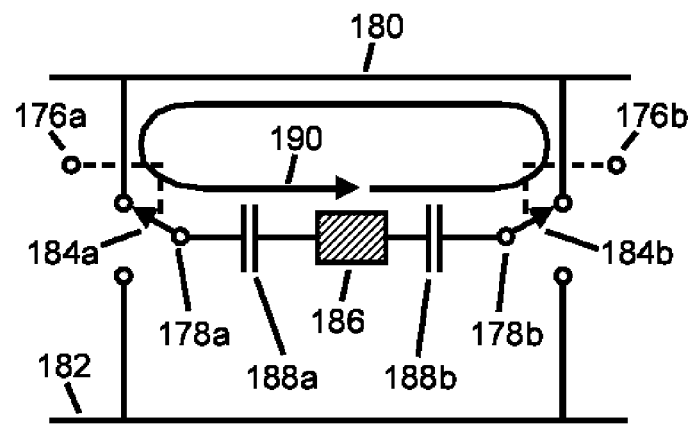
Figure 7D:
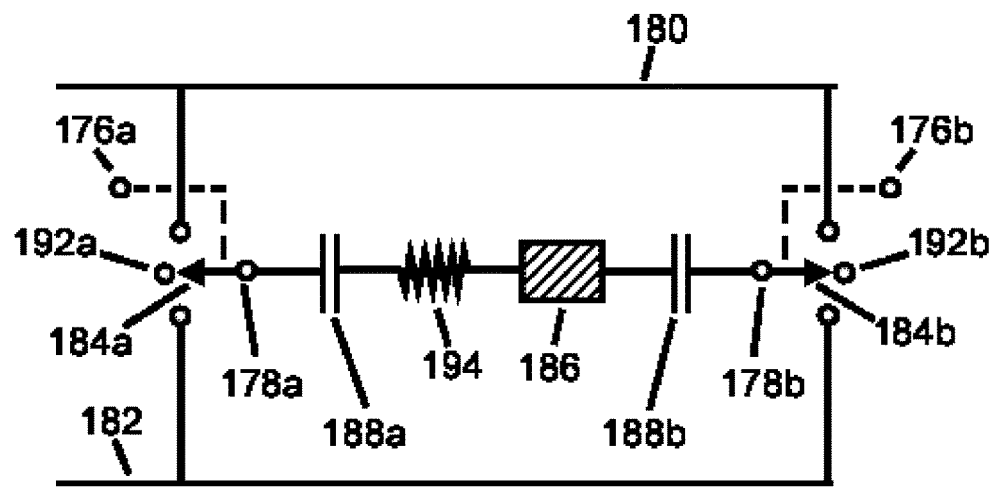

A first preferred embodiment of the invention comprises an output circuit substantially as shown in FIG. 7d, including on each side of the load and optional DC-blocking capacitors a device or configuration of devices having the ability to switch between "high" and "low" logic states and also, in at least one such device or configuration of devices, the ability to enter a high-impedance or "off" state in which substantially zero current flows regardless of any stored charge on the output capacitors; the needed timing and driving circuitry; and sequencing capability embodied either in hardware, in software or in a combination of the two in order to implement the at least three distinct intervals of time described in the Summary of the Invention, to wit: said first interval having one definite polarity and sufficient current density and duration to cause motion of calcium ions ($Ca^{++}$) in relation to less strongly charged components of a body, cell or tissue, such as proteins and especially the protein calmodulin (CaM); said second interval having substantially zero current density and sufficient duration to allow any proteins which became distorted by electric fields present during said first interval, and especially CaM, to relax back into their normal, undistorted shapes, said first and second intervals thus comprising the "two-step electric process" described above; said third interval having one definite polarity opposite that of the first and containing approximately equal charge, having either a like duration and the same (although opposite) intensity, or otherwise; and said fourth interval, if present, again having substantially zero current density and being of sufficient duration to allow any proteins which became distorted by electric fields present during said third interval, again to relax back into their normal, undistorted shapes, said third and fourth intervals thus comprising again the "two-step electric process" described above; in which said signal is intended for application to the human or animal body, to tissues, cells or other biological material through electrodes, such as skin-contact electrodes, or by other conductive means with no reliance on electromagnetic induction; and in which the purpose of said application is one or more of stimulating healing, cell or tissue repair or regeneration, cell proliferation, cell differentiation, enhanced synthesis of desired substances such as proteins, ATP, growth factors, nitric oxide and/or other biochemical messenger substances, or other applications as will be found by reading the cited patents; together with preferred embodiments in the form of electronic circuitry for carrying out said signal generation and application.

Fast switching back and forth between low-impedance states having desired polarities, and high-impedance states resulting in substantially zero current, may be achieved actively and under external control by using any of several electronic circuit components or configurations well-known in the art of digital, analog and especially mixed-signal design. The principle is especially well-known in the art of motor control, since motors appear electrically as inductive loads and as previously stated, when driving such a load with a pulsed signal it is often desirable to add a "break" of high impedance between pulses to ensure that the current from one pulse has dropped to zero before the next pulse is triggered, so successive pulses do not overlap.

Components and configurations able to perform switching functions including high-impedance "breaks" include motor driving circuits, such as the L620x full-bridge motor drivers; pairs of discrete bipolar transistors, MOSFET's or other switching devices, such as the complementary MOSFET pair contained in a NTZD3155C package, plus drivers arranged in the same general configuration; tri-state logic buffers, such as the CD4503B hex CMOS tri-state buffer; analog switches, such as the CD4016B quad analog switch/quad multiplexer, 4051B eight-channel analog multiplexer/demultiplexer, CD4052B dual four-channel analog multiplexer/demultiplexer and CD4053B triple two-channel analog multiplexer/demultiplexer; and other solid-state switching devices having the same general characteristics. In any of these cases, an extra "enable," "disable" or "inhibit" input to the device is required to control switching between the high- and low-impedance output states.

Figure 9:
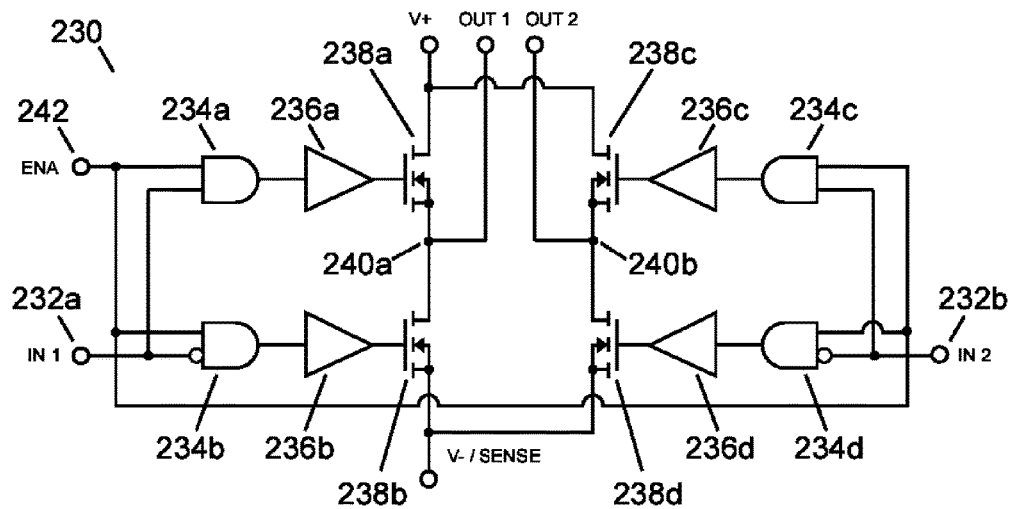
FIG. 9 shows a typical switching circuit configuration used in motor control.

As an example of this action, the L6201 full-bridge motor driver may be analyzed. FIG. 9 shows a somewhat simplified schematic diagram 230 of this device, redrawn from the manufacturer's data sheet. "IN 1" input 232a acting through NAND gates 234a and 234b, to the second of which it is applied through an inverting input as indicated by the small circle, generates complementary outputs from these two gates. Level-shifting amplifiers 236a and 236b adapt these signals to control two n-channel power MOSFET's 238a and 238b, turning one of them on and the other simultaneously off. As a result the voltage at node 240a between them, and thus at the output terminal "OUT 1," takes a value roughly equal to the positive supply voltage when "IN 1" is at logic "high," but roughly equal to the negative supply voltage when "IN 1" is at logic "low."

"IN 2" input 232b, through logic gates 234c and 234d, amplifiers 236c and 236d and MOSFET's 238c and 238d, works in an identical fashion, yielding an output at node 240b and terminal "OUT 2" roughly equal to the positive supply voltage when "IN 2" is at logic "high" but to the negative supply voltage when "IN 1" is at logic "low."

As a result, the L6201 is able to drive a load, normally a small DC-operated motor, connected between its two outputs whenever "IN 1" and "IN 2" differ in polarity, in either a forward or a reverse direction depending upon which one of them is at logic "high." Steady-state currents up to one ampere in either direction are achievable. (Still higher currents are available from other members of the L260x family, the L2602 and L2603.) When both inputs are held in the same logic state, either both "high" or both "low," the outputs are placed at equal corresponding voltages and are substantially shorted together.

So far, the operation of the L6201 is virtually identical with that of the output stages of the previously patented Kronberg electromedical devices, as represented in FIG. 7b, except for its higher voltage- and current-handling capabilities.

The L6201 does, however, have one additional feature not present in those devices: an extra, "ENA" or "enable" input 242. This input is connected to all four NAND gates 234a through 234d, in such a way that when it is held at logic "high" the gates pass signals through from inputs "IN 1" and "IN 2" and the integrated circuit as a whole functions as just described. When "ENA" is held at logic "low," however, all four NAND gate outputs are forced low, and all four MOSFET's turned off. This places the outputs at high impedance, preventing any significant current from flowing through them, and thus is equivalent to the circuit represented in FIG. 7d with both switches in their center, "off" positions.

The transitions between low and high output voltages and between low and high impedance in the L6201 all take roughly the same amount of time, between 200 and 400 nanoseconds: a negligibly small fraction of the (typically) ten to two hundred microseconds required for each pulse phase in a Pilla-type waveform.

Two problems with motor drivers, such as the L6201, make them unsuitable at least for low-powered, battery-driven operation. These are their relatively high supply voltage and current requirements. The L6201 is designed for best operation at 36 volts, can be used up to 48 volts but down only to twelve volts, so any device using it (or any similar device) will need to include batteries providing at least this much voltage. When powered at the recommended 36 volts, the L6201 draws about ten milliamperes for its own operation, exclusive of any current delivered to the load. Another circuit, therefore, more economical of voltage and current, is desirable.

Similar circuit functions could be implemented with lower voltage and current requirements, for example, using separate, discrete but complementary n-channel and p-channel MOSFET's, such as the pair housed in an ON Semiconductor NTZD3155C package, or other transistors. These might be driven either directly by the outputs of a microprocessor or microcontroller, or otherwise through logic gates arranged much as in the L6201. A pair would be required for each side of the load. When designing any such circuit "from scratch," however, much optimization may be needed to assure balanced operation and to prevent "shoot-through": a condition in which both transistors become simultaneously turned on, shorting out the power supply and likely destroying themselves through excessive heating.

Alternatively, a tri-state data buffer, such as one of the gates in a CD4503 package might be used to supply each side of the load. The CD4503, intended as a data bus transceiver, has "data" and "enable" inputs analogous to those of the L6201 but is made to operate at lower voltages and to require vanishingly small supply currents. Its operation is very fast, requiring only a few tens of nanoseconds to switch between high and low output voltage or impedance. Its rated steady-state current output, however, is only 3.7 milliamperes: undesirably low for use in electrostimulators, unless multiple devices are connected in parallel.

While their internal circuitry is considerably more complex than in the devices previously discussed, analog switches and multiplexers such as the CD4016B, CD4051B, CD4052B and CD4053B offer a range of suitable compromises. As shown conceptually in FIG. 10, each of these devices implements, at least to a close approximation, the function of a simple mechanical switch but with the advantages of compactness, logic-level electronic control, and fast response, typically in less than a microsecond, making them well-suited for use in the invention. Their operation is guaranteed over a supply-voltage range from three to twenty volts, and just as in the CD4503, their steady-state operating currents are vanishingly small.

Figure 10:
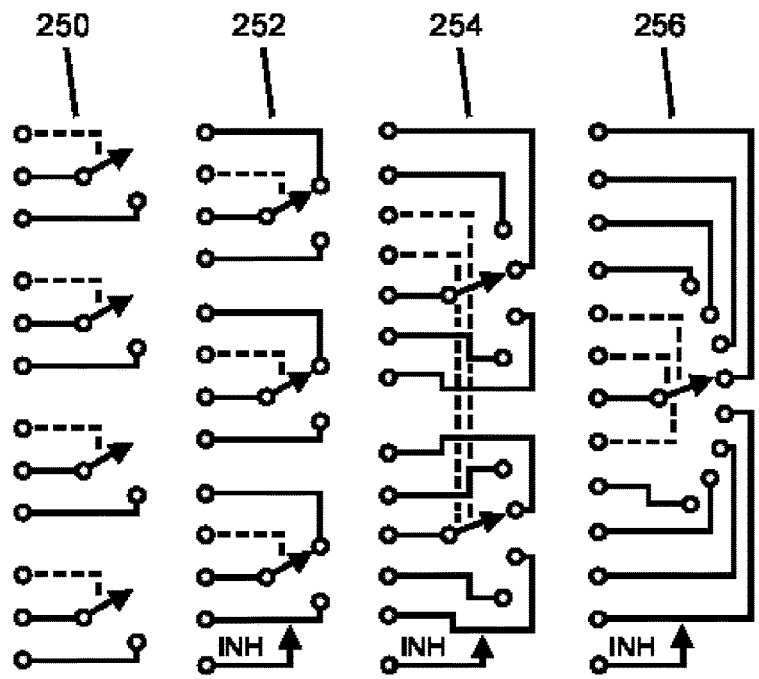
FIG. 10 shows simple conceptual designs for commercially available analog switches and multiplexers.

In FIG. 10, and in increasing order of internal complexity, component group 250 represents the CD4016B with four separately controlled, single-pole single-throw switches; component group 252 represents the CD4053B, with three separately controlled, single-pole double-throw switches; component group 254 represents the CD4052B, with two single-pole, four-position switches controlled in tandem by two binary inputs; and component group 256 represents the CD4051B, with one single-pole, eight-position switch controlled by three binary inputs. Except for the CD4016B, each of these also includes a dedicated "inhibit" (INH) input which when brought to logic "high" places all outputs in a high-impedance state. When using the CD4016, the same could be accomplished by connecting two switches together, one to "high" and the other to "low," then turning on the appropriate one for either desired polarity at low impedance, or leaving both turned off for a high-impedance output.

In using any such analog switching device in a signal generator according to the present invention, the "disable" or "inhibit" input, when held at logic "low," would first allow the passage of current through a selected switch, thus implementing the first step in the "two-step electric process"

described above. The "disable" or "inhibit" input would then be switched to logic "high," stopping the passage of current and thus implementing the second step in the "two-step electric process." Successive alternations of these two states, combined with suitably chosen inputs of alternating polarity to the "data" or "switch common" inputs, would generate any of the waveforms described above.

Figure 11:
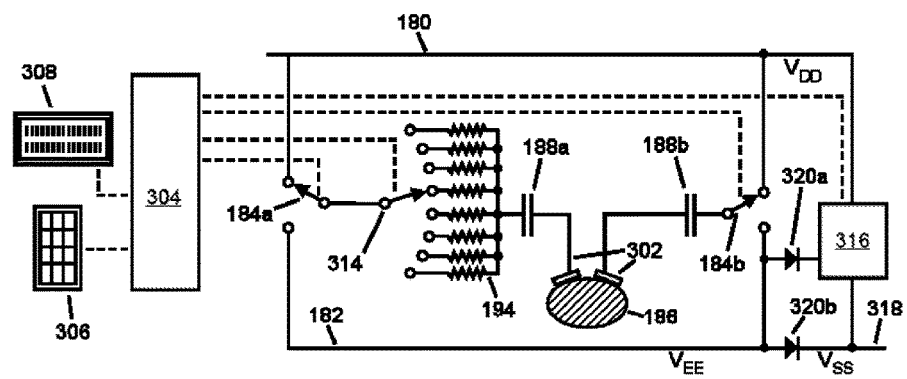
FIG. 11 shows the block diagram of a first preferred embodiment of the invention, using active impedance switching.

A first preferred embodiment 300 of the invention, therefore, shown as a block diagram in FIG. 11, comprises two analog switches 184a and 184b, such as two sections of a CD4053B triple single-pole, double-throw analog switch as described above, configured as was shown in FIG. 7d with DC-blocking capacitors 188a and 188b and means 302, such as wires and skin electrodes, for connection to an external load 186 such as a human or animal body, tissues, cells or other biological material for purposes of stimulation or pain relief as previously described. Timing is provided by control block 304, which may be either analog, digital, or a combination of both. For example, in a partly analog implementation block 304 could be comprised partly of TLC-555 or equivalent, integrated timing circuits with or without auxiliary logic circuitry, substantially as described in Kronberg prior art U.S. Pat. No. 5,217,009. Alternatively and more preferably, block 304 could consist of digital counting and timing circuitry substantially as described in Kronberg prior art U.S. Pat. No. 5,413,596. Most preferably, block 304 consists of a microprocessor or microcontroller which not only provides the timing functions, but also interfaces with a user input section 306, such as a keypad, and a user display section 308, such as a liquid-crystal display.

Figure 12:
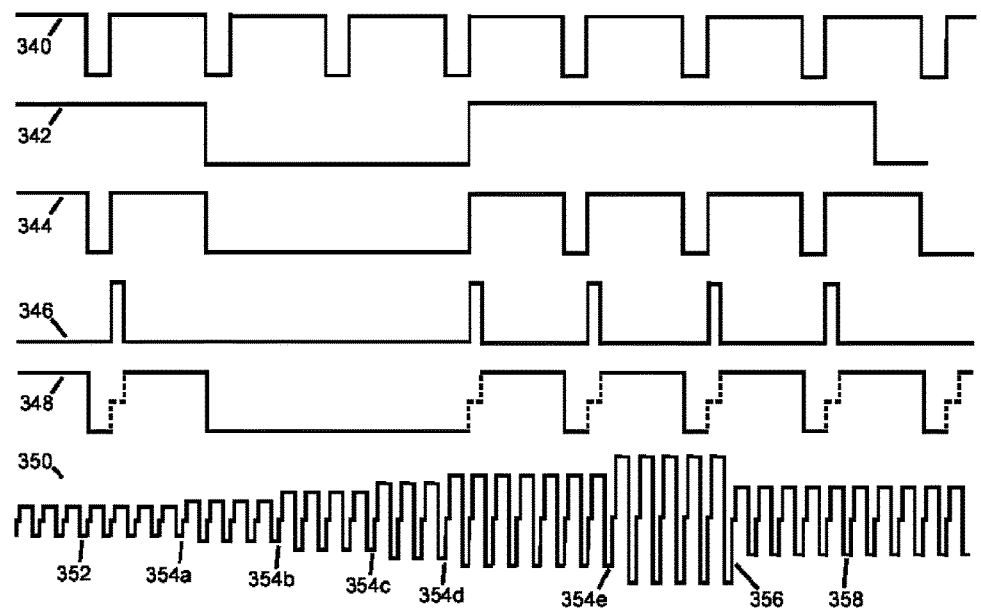
FIG. 12 shows waveforms associated with the first preferred embodiment of the invention.

Typical waveforms associated with first preferred embodiment 300 are shown in FIG. 12. A first digital logic signal 340, comprising the pulse phase envelope, is generated by control block 304 and, if a pulse-burst signal rather than a continuous pulse train is required, is modulated by a second digital logic signal 342 comprising the pulse burst envelope yielding a modulated signal 344. An "inhibit" signal 346 may be generated either by the same digital timing circuitry in block 304 which generates signal 340, or from signal 340 or signal 344 by external means. For example, a simple R-C network may be used to generate a short, CMOS-compatible positive pulse upon each rising edge of signal 340 or 344. If connected to the "inhibit" input of a digitally-controlled analog switch such as the CD4053B, during each such pulse this signal changes the output to high impedance. (Conceivably, a different type of analog switch might be used which, because of circuit differences, required a logic low signal to inhibit the output. This could be provided by adding a simple inverting logic gate to the circuit.)

Figure 8:
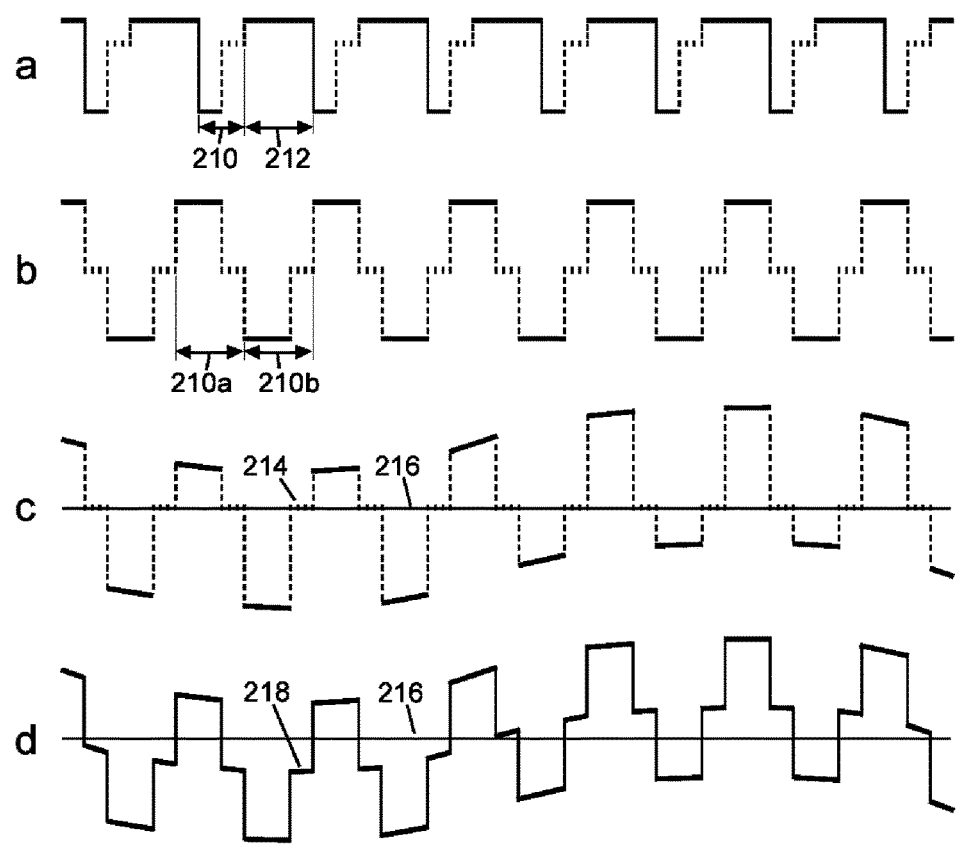
FIG. 8 shows a comparison of waveforms according to the present invention with those of prior art.

The combined effect of these components and control signals is to produce an output signal 348 in load 186. The same notation is used as in FIG. 8, with dashed lines indicating the intervals of high impedance and the adjacent transitions. For purposes of illustration and easy comparison with the Kronberg and Pilla prior art, the waveforms shown correspond to an asymmetric pulse-burst waveform in which the "two-step electric process" occurs only once per pulse, after the shorter and more negative phase. Obviously, however, the same principles apply to either a symmetric or asymmetric, pulse-burst or pulse train waveform regardless of the number of repetitions of the "two-step electric process" per pulse.

Optionally, a second digitally-controlled analog switch 314, such as a CD4051B, may be used under the control of block 304 to control the signal intensity through selection of one from a plurality of resistors as indicated, for purposes of illustration, by the block of eight resistor symbols 194 in FIG. 11. The resistance values may be selected to make the successive steps between signal intensity levels linear, exponential, or having any other desired relationship. Alternatively, a digital potentiometer having a large number of possible resistances might take the place of switch 314 and resistor block 194.

In addition, a voltage-converting circuit 316, such as a TC7660 charge pump, or a plurality of such circuits may be used to change the voltage applied between supply rails 180 and 182, and may be switched on and off by control block 304 during operation as desired. For example, an initial and larger voltage difference might be used to allow initial sensation by the patient to assure correct operation and connection. The voltage might then be decreased, for instance by turning off circuit 316, to provide a correct, sub-sensory-threshold signal for tissue stimulation.

The CD405xB series of analog switches offers an optional negative voltage rail input $V_{EE}$, permitting balanced operation around a common supply rail 318 which is "center ground" for the analog signals being switched while also serving as the negative logic rail $V_{SS}$. This permits the analog signals being switched to take any value within the range from the positive voltage $V_{DD}$ on rail 180, down to $V_{EE}$, inclusive. When no voltage more negative than common is used, the $V_{EE}$ and $V_{SS}$ pins are simply tied together. To take full advantage of this feature, circuit 316 is here shown as a negative voltage converter providing an output of approximately $-V_{DD}$, with diodes 320a and 320b selecting as $V_{EE}$ for switches 184a, 184b and 314 on rail 182 either the "common" voltage $V_{SS}$ from rail 318, or the output from circuit 316 when it is turned on by control block 304, whichever is the more negative.

Examples of these intensity changes, not drawn to scale in time, are shown by trace 350 in FIG. 12. In order to show operation over a large number of pulses, a continuous pulse-train signal is shown instead of the pulse-burst one of the previous traces in this Figure, at higher frequency and without specific notation identifying the different impedance levels in each pulse.

At power-up, control block 304 selects a high resistor value from among those in block 194 and turns on voltage converter 316, providing an initial subthreshold signal level 352. This level is then adjusted upward in steps 354a, 354b and so forth by a patient, for example through keystrokes on pad 306, selecting successively lower-valued resistors in block 194 with resulting higher intensities, until a faint sensation can be felt assuring the patient that the signal generator and electrodes are functioning correctly. After a short interval following the last keypress, at time 356 control block 304 turns off converter 316, lowering the signal intensity again to a subthreshold level 358 for treatment. (Alternatively, control block 304 could perform this action by selecting a different resistance value from block 194, or by a combination of voltage reduction with such selection.)

Figure 13:
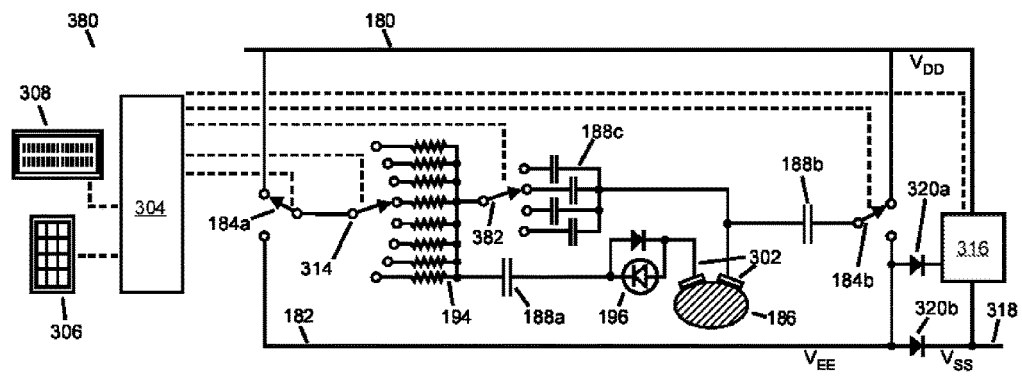
FIG. 13 shows the block diagram of a second preferred embodiment of the invention, using passive impedance switching.

A second preferred embodiment 380 of the invention, shown as a block diagram in FIG. 13, differs from the first only in that the high-impedance interval of each iteration of the "two-step electric process" is provided through one or more nonlinear devices 196 placed in series with load 186, plus a capacitor or combination of capacitors 188c and an optional additional multiposition analog switch 382, together connected in parallel with the load and these devices.

Figure 7E:
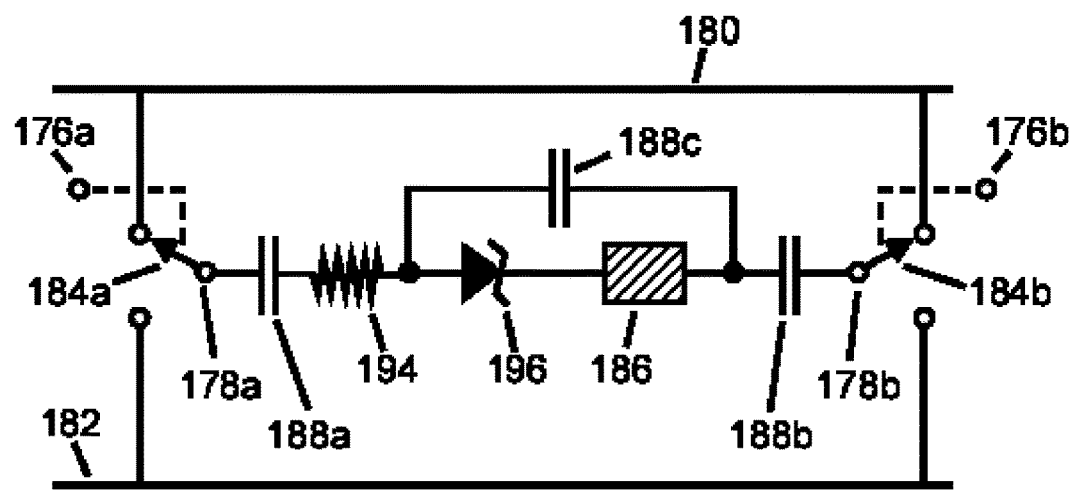
Figure 7F:
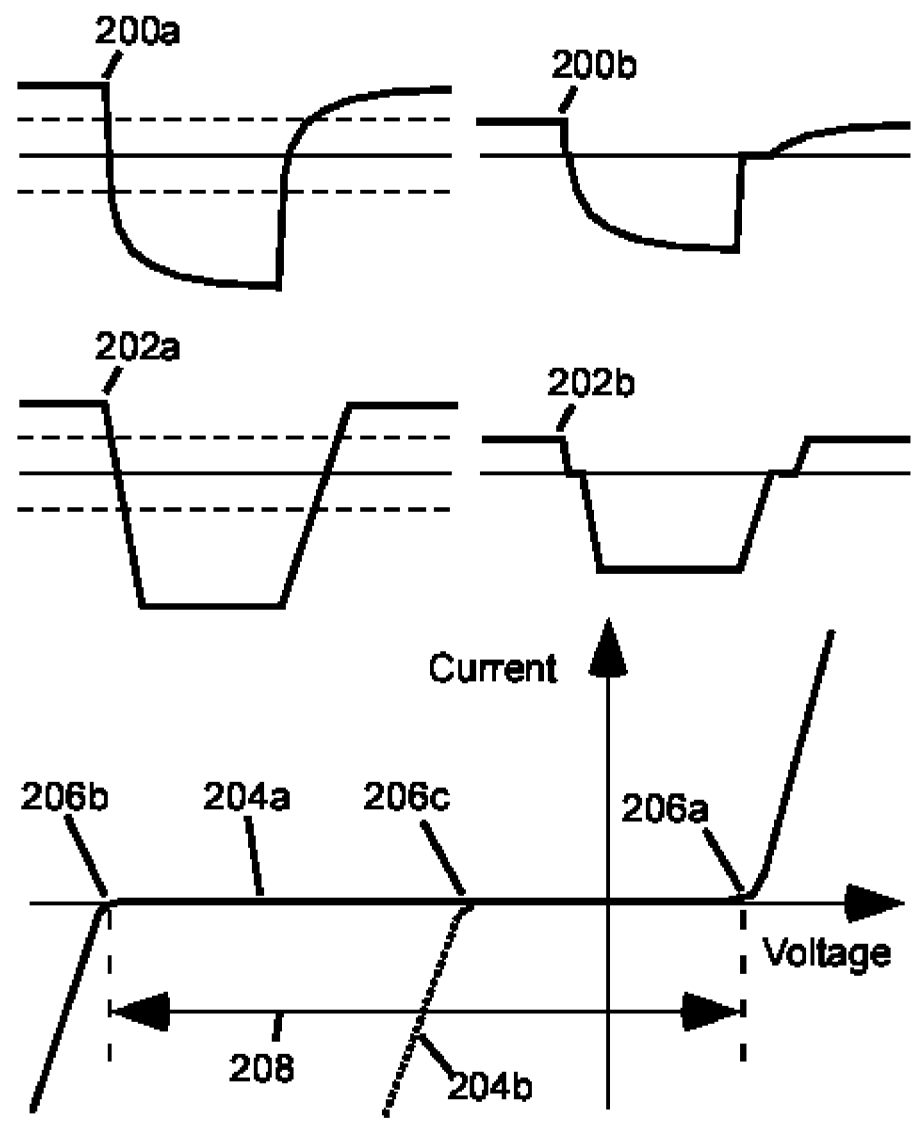

Together, these added devices function as previously shown and explained in FIG. 7e, 7f and the accompanying text, rendering all transitions between voltage and current levels more gradual while switching to high impedance with substantially zero output voltage or current as the voltage across capacitor 188*c* passes through a range close to and including zero. Nonlinear device or devices 196 are here represented by a pair of diodes connected head-to-tail, and shown with slightly different symbols (one suggesting a simple rectifier, the other suggesting an LED) to emphasize that if multiple devices are used they need not all be of the same type, technology or material provided they have the general characteristics shown in FIG. 7*f.*

So that each intensity setting selected by switch 314 will have approximately the same R-C time constant, thus maintaining a constant proportionality between constant and ramped portions of the signal, or so that approximately the same proportion of time will be spent by the signal at each intensity level while crossing the voltage range corresponding to high output impedance, a plurality of capacitive elements 188*c* may be provided and connected to analog switch 382 in the same manner as the resistive elements are connected to switch 314, both switches then being controlled by digital selection inputs from block 304 so that for each resistive element of 194 or subset of said elements, a different value of capacitance is selected from block 188*c* to provide the desired R-C time constant.

If it is not desired to select different capacitive values for different resistive ones, switch 382 and plurality of capacitors 188*c* may be replaced by a single, fixed capacitor. Alternatively, each of resistors 194 may be placed individually in series with its own capacitor, or one or more subsets of these resistors grouped with their ends tied together (much as all eight resistors are grouped in FIG. 13), for example in two groups of four resistors each, and each said group placed in series with its own capacitor, said capacitors then replacing group 188*c* without the intervention of switch 382.

To maintain a solid DC connection between analog switches 314 and 382 and rails 180 and 182, so that the only voltages seen by the switches lie in the range between or including $V_{DD}$ and $V_{EE}$, DC-blocking capacitor 188*a* has also been moved to the opposite side of load 186, next to capacitor 188*b*. This has no impact on the ability of these capacitors to block DC from load 186, since they and the load are all connected in series and thus carry identical AC and, were they not suppressed by the capacitors, also DC currents.

Figure 14:
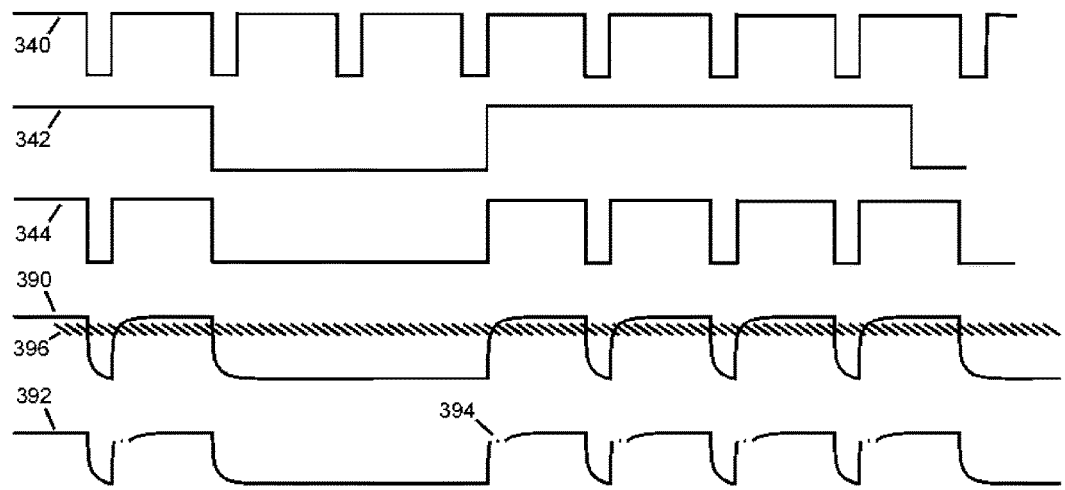
FIG. 14 shows waveforms associated with the second preferred embodiment of the invention.

Typical waveforms associated with second preferred embodiment 380 are shown in FIG. 14. As in the first preferred embodiment, a first digital logic signal 340, comprising the pulse phase envelope, is generated by control block 304 and, if a pulse-burst signal rather than a continuous pulse train is required, is modulated by a second digital logic signal 342 comprising the pulse burst envelope yielding a modulated signal 344. No "inhibit" control signal, however, is generated. Instead, modulated signal 344 is acted upon by resistive elements 194 and capacitive elements 188*c* producing a signal 390 having more gradual transitions. Passage of signal 390 through nonlinear elements 196 then yields a signal 392 having periods of high impedance such as 394 whenever the signal voltage passes through near-zero region 396 of signal 390 defined by the cut-in voltages of device or devices 196.

By making pulse phase envelope signal 340 as asymmetrical as other circuit factors and signal requirements permit, once DC components of the signal are blocked the zero level, and hence region 396 surrounding it, are shifted toward the level of the longer pulse phase since for zero net charge overall, the longer phase must be of lower intensity than the shorter one to contain equal and opposite charge. This means that when the transition between phases is exponentially decaying, as it is when implemented using resistors and capacitors as shown, upon transition from the shorter to the longer phase the passage through near-zero region 396 will be relatively slow and thus high-impedance regions 394 will be relatively long compared to those seen upon the opposite transition or when signal 340 is more symmetrical. A preferable ratio of phase lengths in signal 340 is from about 3:1, as shown in FIG. 14, up to about 20:1, while a more preferable ratio is likely in the vicinity of 7:1. The exact ratio can be found through a modest amount of experimentation once devices 196 have been selected or, conversely, this ratio and the duration of the high-impedance interval may first be defined and then an optimal selection of devices 196 made, again likely through a modest amount of experimentation.

Certain steps in the processes or process flows described in this specification naturally precede others for the invention to function as described. However, the invention is not limited to the order of the steps described if such order or sequence does not alter the functionality of the invention. That is, it is recognized that some steps may performed before, after, or parallel (substantially simultaneously with) other steps without departing from the scope and spirit of the invention. In some instances, certain steps may be omitted or not performed without departing from the invention. Further, words such as "thereafter", "then", "next", etc. are not intended to limit the order of the steps. These words are simply used to guide the reader through the description of the exemplary method.

Additionally, one of ordinary skill in programming is able to write computer code or identify appropriate hardware and/or circuits to implement the disclosed invention without difficulty based on the flow charts and associated description in this specification, for example. Therefore, disclosure of a particular set of program code instructions or detailed hardware devices is not considered necessary for an adequate understanding of how to make and use the invention. The inventive functionality of the claimed computer implemented processes is explained in more detail in the above description and in conjunction with the drawings, which may illustrate various process flows.

In one or more exemplary aspects, the functions described may be implemented in hardware, software, firmware, or any combination thereof. If implemented in software, the functions may be stored on or transmitted as one or more instructions or code on a computer-readable medium. Computer-readable media include both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a coaxial cable, fiber optic cable, twisted pair, digital subscriber line ("DSL"), or wireless technologies such as infrared, radio, and microwave, then the coaxial cable, fiber optic cable, twisted pair, DSL, or wireless technologies such as infrared, radio, and microwave are included in the definition of medium.

Disk and disc, as used herein, includes compact disc ("CD"), laser disc, optical disc, digital versatile disc ("DVD"), floppy disk and blu-ray disc where disks usually reproduce data magnetically, while discs reproduce data optically with lasers. Combinations of the above should also be included within the scope of computer-readable media.

Although a few embodiments have been described in detail above, those skilled in the art will readily appreciate that many modifications are possible in the embodiments without materially departing from this disclosure. Accordingly, such modifications are intended to be included within the scope of this disclosure as defined in the following claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, sixth paragraph for any limitations of any of the claims herein, except for those in which the claim expressly uses the words 'means for' together with an associated function.

Alternative embodiments will become apparent to one of ordinary skill in the art to which the invention pertains without departing from its spirit and scope. Therefore, although selected aspects have been illustrated and described in detail, it will be understood that various substitutions and alterations may be made therein without departing from the spirit and scope of the present invention, as defined by the following claims.

What is claimed is:

1. A method for generating and applying a bioelectric signal to a biologic material, the method comprising the following steps applied in sequence:
    generating at least one pulse of a pulse burst of the bioelectric signal by:
        applying an electrical current to the biological material for a first interval of time and in a first direction;
        holding the electrical current at a substantially zero amplitude for a second interval of time resulting in substantially zero electrical current, the electrical current at a substantially zero amplitude allowing molecules of calmodulin in the biological material, when distorted by voltage gradients of the applied electrical current during the first interval of time, to relax back into their normal, undistorted shapes during the second interval of time, thus restoring any lost ion-binding capacity and permitting said calmodulin to bind calcium ions before the electrical current is reapplied for a third interval of time;
        during said second interval of time, where the electrical current is held at the substantially zero amplitude, results in substantially no electrical current; and when the second interval of time is plotted as a waveform, the waveform comprises a distinct flattening in every rising or falling edge of the waveform as an amplitude of the electrical current passes through a zero level, said second interval of time having a duration shorter than either of said first and third intervals of time;
        applying the electrical current to the biological material for the third interval of time and in a second direction, the second direction being opposite to the first direction of the first interval, the electrical current during the third interval bringing fresh calcium ions into close proximity with said calmodulin; and
    repeating the steps for a plurality of times in order to form a succession of pulse bursts, wherein said pulse bursts are separated by an interburst interval held at a substantially zero amplitude for an interval of time substantially longer than the a sum of said first, second and third intervals of time.

2. The method of claim 1, further comprising: generating the bioelectric signal by one or more electronic components connected in electrical series with said biological material, said one or more electronic components having impedances which are lower during intervals with electrical current than during intervals with substantially no electrical current.

3. The method of claim 2, wherein said one or more electronic components have low impedance during said first and third intervals of time, thereby permitting free flow of electrical current to said biological material, but said one or more electronic components change to higher impedance during said second interval of time, thereby substantially blocking said electrical current from flowing to said biological material.

4. The method of claim 3, wherein an impedance change in said one or more electronic components is achieved by applying a control signal.

5. The method of claim 4, wherein said one or more electronic components comprise at least one of: a motor driving circuit; a discrete bipolar transistor, a MOSFET; a tri-state logic buffer; and an analog switch.

6. The method of claim 3, further comprising: achieving the low and high impedance through electrically nonlinear characteristics of said one or more electronic components.

7. The method of claim 6, wherein said one or more electronic components comprise at least one of a diode, a Schottky diode, a junction diode, a Zener diode, an avalanche diode, a light-emitting diode, a disc, and a metal-oxide varistor.

8. The method of claim 1, wherein the duration of at least one of said first, second, and third intervals is between about 0.1 microsecond and about 10,000 microseconds.

9. The method of claim 8, wherein the duration of at least one of said first, second, and third intervals is between about 1.0 microsecond and about 1000.0 microseconds.

10. The method of claim 9, wherein the duration of at least one of said first, second, and third intervals is between about 5.0 microsecond and about 100.0 microseconds.

11. The method of claim 1, wherein the applied electrical current during said first and said third interval creates a maximum electrical current density below about 100.0 microamperes per square centimeter passing in either direction through said biological material.

12. The method of claim 11, wherein said applied electrical current, when summed over at least ten successive complete pulses, results in substantially zero net charge (ZNC) overall.

13. The method of claim 11, wherein said applied electrical current, when summed over at least ten successive complete pulses, does not result in substantially zero net charge overall but instead has a measurable direct current component.

14. The method of claim 11, wherein a maximum value of said electrical current density is set through one or more resistive elements placed in series with said biological material.

15. The method of claim 14, wherein the maximum value of said electrical current density is achieved by a plurality of said one or more resistive elements; and an open circuit or an inhibited output comprising a high-impedance state.

16. The method of claim 15, wherein the maximum value of said electrical current density is achieved with discrete analog or digital logic components.

17. The method of claim 15, wherein the maximum value of said electrical current density is achieved with one or more microprocessors or microcontrollers.

18. The method of claim 14, wherein the maximum value of said electrical current density is achieved with voltage applied to said one or more resistive elements.

19. The method of claim 14, wherein said one or more resistive elements are electrically coupled to capacitors to slow a rise and to slow a fall of voltage, and electrically coupled to one or more devices having electrically nonlinear characteristics so as to create a high-impedance interval as a rise or a fall of the electrical current passes through a near-zero region.

20. The method of claim 1, introducing the bioelectric signal to a human or animal body through electrodes which are at least one of placed on, penetrating, and implanted beneath a skin surface.

21. The method of claim 20, further comprising placing the electrodes in body locations typically having lower-than-average electrical resistance.

22. The method of claim 21, further comprising placing the electrodes according to at least one of a chart of trigger points for a human body; a chart of acupuncture points for a human body: and points typically having lower-than-average electrical resistance for a human body.

23. The method of claim 1, further comprising generating the bioelectric signal using power from a battery.

24. The method of claim 1, further comprising generating the bioelectric signal using an AC-to-DC power converter comprising a "wall wart" type modular power supply.

25. The method of claim 1, further comprising generating the bioelectric signal using power provided from at least one of a photovoltaic cell, a fuel cell, and wireless power transfer.

26. The method of claim 1, further comprising forming at least one of a power supply for the bioelectric signal and an electrode for the bioelectric signal such that at least one of the power supply and the electrode form part of an article of clothing.

* * * * *